US011944288B2

(12) United States Patent
Allen et al.

(10) Patent No.: US 11,944,288 B2
(45) Date of Patent: Apr. 2, 2024

(54) TISSUE ANCHOR SYSTEM INCLUDING A FIXATION DEVICE AND A DELIVERY TOOL

(71) Applicant: Coloplast A/S, Humlebaek (DK)

(72) Inventors: John J. Allen, Mendota Heights, MN (US); John Clegg, Minneapolis, MN (US); William Hartsig, Hudson, WI (US); Peter Meinz, Minneapolis, MN (US); Mark A. Moschel, Plymouth, MN (US); Sarah J. Schuchardt, Minneapolis, MN (US)

(73) Assignee: Coloplast A/S, Humlebaek (DK)

( * ) Notice: Subject to any disclaimer, the term of this patent is extended or adjusted under 35 U.S.C. 154(b) by 290 days.

(21) Appl. No.: 17/242,329

(22) Filed: Apr. 28, 2021

(65) Prior Publication Data

US 2021/0338226 A1   Nov. 4, 2021

Related U.S. Application Data

(60) Provisional application No. 63/122,496, filed on Dec. 8, 2020, provisional application No. 63/017,030, filed on Apr. 29, 2020.

(51) Int. Cl.
    *A61B 17/04* (2006.01)
(52) U.S. Cl.
    CPC .. *A61B 17/0401* (2013.01); *A61B 2017/0409* (2013.01); *A61B 2017/0412* (2013.01); *A61B 2017/0414* (2013.01); *A61B 2017/0427* (2013.01); *A61B 2017/0464* (2013.01)

(58) Field of Classification Search
    CPC .... A61B 2017/0409; A61B 2017/0412; A61B 2017/0414; A61B 2017/0427; A61B 2017/0464
    See application file for complete search history.

(56) References Cited

U.S. PATENT DOCUMENTS

| 5,041,129 | A | * | 8/1991 | Hayhurst | A61B 17/0401 606/220 |
|---|---|---|---|---|---|
| 5,894,921 | A | | 4/1999 | Le et al. | |
| 6,502,578 | B2 | | 1/2003 | Raz et al. | |
| 6,506,197 | B1 | | 1/2003 | Rollero et al. | |
| 6,595,911 | B2 | | 7/2003 | Lovuolo | |
| 6,641,524 | B2 | | 11/2003 | Kovac | |
| 6,695,855 | B1 | | 2/2004 | Gaston | |
| 7,320,701 | B2 | | 1/2008 | Haut et al. | |
| D572,546 | S | | 7/2008 | Stahm | |
| 7,914,437 | B2 | | 3/2011 | Gozzi et al. | |
| 8,409,075 | B2 | | 4/2013 | Chu | |

(Continued)

FOREIGN PATENT DOCUMENTS

| CA | 2665934 | 4/2008 |
|---|---|---|
| EP | 1484022 B1 | 6/2008 |

(Continued)

*Primary Examiner* — Alexander J Orkin
(74) *Attorney, Agent, or Firm* — Coloplast Corp., Coloplast A/S; Nick Baumann

(57) ABSTRACT

A tissue anchor system includes a fixation device and a tool. The fixation device includes a tab connected to a tissue anchor. The tool includes a shaft connected between a proximal handle portion and a distal tip. The distal tip is configured to limit movement of the fixation device during loading of the tissue anchor.

25 Claims, 26 Drawing Sheets

(56) References Cited

U.S. PATENT DOCUMENTS

| | | | |
|---|---|---|---|
| 8,579,797 B2 | 11/2013 | Arnal et al. | |
| 8,771,314 B2 | 7/2014 | Crombie et al. | |
| 9,198,747 B2 | 12/2015 | De Leval | |
| 9,510,822 B2 | 12/2016 | Poucher et al. | |
| 9,517,130 B1* | 12/2016 | Alon | A61F 2/2442 |
| 9,877,818 B2 | 1/2018 | Poucher et al. | |
| 2002/0019649 A1 | 2/2002 | Sikora et al. | |
| 2004/0002734 A1 | 1/2004 | Fallin et al. | |
| 2004/0138704 A1* | 7/2004 | Gambale | A61B 17/1114 |
| | | | 606/213 |
| 2004/0243178 A1 | 12/2004 | Haut et al. | |
| 2005/0019368 A1 | 1/2005 | Cook et al. | |
| 2006/0030884 A1 | 2/2006 | Yeung et al. | |
| 2009/0041548 A1 | 2/2009 | Stahm | |
| 2009/0137862 A1 | 5/2009 | Evans et al. | |
| 2009/0171143 A1 | 7/2009 | Chu et al. | |
| 2010/0105979 A1 | 4/2010 | Hamel et al. | |
| 2010/0191045 A1 | 7/2010 | Gobron et al. | |
| 2010/0197999 A1 | 8/2010 | Deegan et al. | |
| 2010/0269422 A1 | 10/2010 | Stahm | |
| 2011/0022061 A1 | 1/2011 | Orphanos et al. | |
| 2011/0218387 A1 | 9/2011 | Lamson et al. | |
| 2011/0297161 A1 | 12/2011 | Deitch | |
| 2011/0306992 A1* | 12/2011 | Darois | A61B 17/0401 |
| | | | 606/145 |
| 2012/0035654 A1 | 2/2012 | Belson | |
| 2013/0006045 A1 | 1/2013 | Deitch et al. | |
| 2013/0012765 A1 | 1/2013 | Vemuri et al. | |
| 2013/0023724 A1 | 1/2013 | Allen et al. | |
| 2013/0238023 A1 | 9/2013 | Wales et al. | |
| 2013/0245700 A1 | 9/2013 | Choinski | |
| 2013/0253260 A1 | 9/2013 | Lund et al. | |
| 2013/0325063 A1 | 12/2013 | Norton et al. | |
| 2014/0128914 A1 | 5/2014 | Deitch et al. | |
| 2015/0250470 A1* | 9/2015 | Vargas | A61B 17/0401 |
| | | | 606/232 |
| 2015/0297333 A1 | 10/2015 | Poucher et al. | |
| 2016/0157980 A1* | 6/2016 | Poucher | A61B 17/06166 |
| | | | 600/30 |
| 2017/0245974 A1 | 8/2017 | Poucher et al. | |
| 2018/0228597 A1 | 8/2018 | McCarty, III | |
| 2019/0328380 A1 | 10/2019 | Poucher et al. | |
| 2020/0360007 A1* | 11/2020 | Cunningham | A61B 17/0401 |

FOREIGN PATENT DOCUMENTS

| | | |
|---|---|---|
| EP | 2134265 B1 | 6/2012 |
| EP | 2543341 B1 | 7/2016 |
| EP | 2740415 B1 | 2/2017 |
| EP | 2727539 B1 | 1/2018 |
| EP | 2277456 B1 | 4/2018 |
| EP | 3028649 B1 | 8/2018 |
| WO | 2007097994 A2 | 8/2007 |
| WO | 2008107026 A2 | 9/2008 |
| WO | 2010062851 A1 | 6/2010 |
| WO | 2013006866 A1 | 1/2013 |
| WO | 2013044228 A1 | 3/2013 |

* cited by examiner

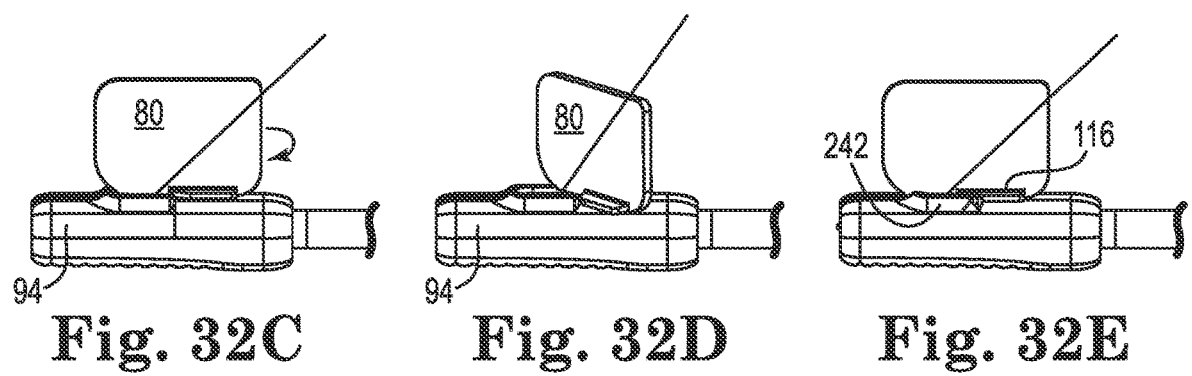
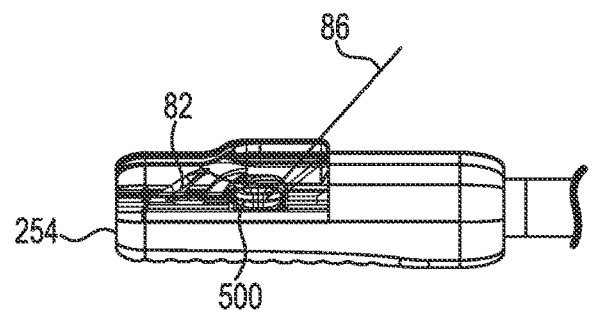

TISSUE ANCHOR SYSTEM INCLUDING A FIXATION DEVICE AND A DELIVERY TOOL

BACKGROUND

Repair of the structural integrity of the pelvis includes the implantation of biological grafts or native tissue repair to treat organ prolapse within the pelvis. The pelvic repairs are facilitated through the placement of anchors to fixate a desired placement of supporting suture. Typically, the anchor is engaged in a tissue landmark like a ligament. The suture extends from the anchor and can be used for native tissue repair or to support a graft. These surgical techniques are usefully employed to treat incontinence, pelvic organ prolapse, and in reconstructing tissue defects.

Improved fixation devices, delivery tools for the fixation devices, and methods of fixating surgical implants would be welcomed by patients and surgeons.

SUMMARY

A system is disclosed that allows tissue repair for patients who are candidates for surgical treatment of pelvic organ prolapse (POP) requiring fixation to tissue including the sacrospinous ligament (SSL), the obturator complex, or the arcus tendineus fascia pelvis (ATFP). The system provides a delivery device that facilitates transvaginal implantation of tissue fixation anchors during pelvic reconstruction, where the anchors provide a support network (for at least suture) for the treatment of pelvic organ prolapse. The transvaginal implantation is considered by some surgeons to be less invasive or minimally invasive as compared to abdominal implantation.

The system provides anchors that are small but that have excellent resistance to pull-out after placement in tissue. The anchors are provided as part of a fixation device where a handling tab is removably attached to the anchor. The handling tab allows a healthcare worker, specifically a healthcare worker wearing gloves, to load the relatively small anchor into the delivery device. After the small anchor is loaded into the delivery device, the tab is removed from the anchor and the tab is discarded.

The tab has a flange connected to and co-planar with an inferior side (or bottom) of the tab, where the flange projects in a lateral direction away from a face of the tab. The flange is part of a guide system to ensures the anchor is aligned properly with the delivery device during loading. The other part of the guide system is a guide rail formed on a surface of the delivery device. The healthcare worker can be assured that the anchor is in proper alignment when the flange is engaged or seated within the guide rail. Movement of the anchor and tab in a proximal direction results in an audible or tactile response (a "click") which indicates the anchor is retained in the delivery device. The proper loading of the anchor as described above results in the flange being positioned in a location clear from the guide rail, which locates the tab in a position to allow the tab to be rotated and separated from the anchor.

Another approach described below is providing the flange as described above along with a second flange. In this case, the tab includes a sled formed by the second flange connected to the inferior side of the tab opposite of the first flange. The second flange projects in a lateral direction away from a second face of the tab, and the first flange projects in a lateral and opposite direction. The sled thus provides a large planar and wide surface at the bottom of the otherwise narrow tab. The sled provides haptic feedback when it properly engages with the guide rails of the delivery device.

The anchor has a large eyelet that accommodates at least two lines of suture of the surgeon's choice as well as any suture needle attached to either of the sutures. A tissue anchor having an eyelet sized for a plurality of sutures and a plurality of needles (i.e., double armed suture) is a distinct advantage to surgeons.

Loading of an anchor as described above prepares the delivery device for the transvaginal repair of pelvic organ prolapse.

Repair of a prolapsed organ within the pelvis can be accomplished through native tissue repair, repair using synthetic grafts, or repair using biological grafts. The grafts would be attached to pelvic landmarks using the delivery device to deliver the anchor and the suture. Native tissue repair does not utilize external grafts. Native tissue repair benefits from the use of the anchor and suture attached to tissue landmarks in the pelvic area to facilitate the restoration of the pelvic floor. Native tissue repair is used in approximately 70% of all POP procedures, and the total number of POP procedures utilizing native tissue repair is expected to continue to increase. The disclosed system is suitable for both native tissue repair and POP repair using biologic or synthetic grafts.

A system is disclosed that allows transvaginal implantation of tissue fixation anchors during pelvic reconstruction, where the anchors provide a support network for the treatment of pelvic organ prolapse. The transvaginal implantation is considered by some surgeons to be less invasive or minimally invasive as compared to abdominal implantation. The system includes a delivery device for placement of anchors into native tissue, where the anchors are configured to couple with any of a variety of sutures of the surgeon's choice during repair of the pelvic floor.

The anchors include a large eyelet that allows a surgeon to attach one or more strands of suture to each anchor. Each anchor is passed through a vaginal incision with a delivery tool and subsequently attached to ligaments or other suitable landmarks within the pelvis. The length of suture trails away from the anchor at the landmark, through the vaginal incision, to a location outside the patient. Several such anchors and associated lengths of suture are delivered into the pelvis. The surgeon completes native tissue repair with the sutures. Alternatively, the surgeon secures a support material to the length(s) of suture and passes the support material into the pelvis through the vaginal incision. The anchors, the length(s) of suture, and the support material (if utilized) combine to provide a support structure to support the pelvic floor and treat POP.

The system includes a tissue fixation device that is inserted into a delivery device. The tissue fixation device includes a tab that is removably secured to the tissue anchor. As noted above, the anchor itself is small and generally difficult to handle with a gloved hand during surgery. The eyelet of the anchor is relatively large compared to the size of the anchor, and the eyelet allows the surgeon to pass one or more suture strands quickly and easily through the eyelet. Those who are familiar with threading suture into needle will understand the benefit of a large eyelet size. The tab attached to the anchor provides a large surface area that facilitates handling of the small anchor. The benefits of the tissue fixation device thus include a large eyelet for easy threading of suture and a large tab for handling the small anchor when inserting it into the delivery device. After the anchor is inserted into the delivery device the tab is detached from the anchor and discarded.

The delivery device (or tool) has a distal tip that securely retains the anchor during the transvaginal procedure. The tool is curved along a selected path to allow the tool to traverse through the pelvis from the vaginal incision to a location of a ligament, for example, a sacrospinous ligament. The curved tool thus has the benefit of securely delivering the tissue anchor through the pelvis to the chosen ligament. The delivery device has a plunger mechanism that is configured to push the anchor into the relatively tough tissue of the ligament.

A first aspect provides a tissue anchor fixation device comprising:
- a tissue anchor comprising a body extending longitudinally between a nose of the tissue anchor and a tail of the tissue anchor, with the nose having a pointed distal end adapted to penetrate tissue and the tail forming an eyelet sized to receive a strand of suture; and
- a tab connected to the tissue anchor, with the tab having a distal side opposed to a proximal side and a superior side opposed to an inferior side, and the tab is adapted to be separated from the tissue anchor;
- wherein the tab comprises a first flange connected to and co-planar with the inferior side of the tab, with the first flange projecting in a lateral direction away from a first face of the tab. The advantage of the first flange is to locate the relatively small anchor in a properly aligned orientation with the distal tip. The first flange is a haptic feature of the small anchor.

An embodiment of the first aspect includes wherein the tab comprises a sled comprising a second flange connected to the inferior side of the tab opposite of the first flange, with the second flange projecting in a lateral direction away from a second face of the tab that is opposite of the first face of the tab. The benefit of the sled is that it allows a user to correctly align the anchor portion for engagement and retention inside of the tool.

An embodiment of the first aspect includes wherein the sled is planar, and co-planar with the inferior side of the tab, such that the sled defines a bottom-most inferior surface of the tab. A benefit of the planar sled is that it provides a haptic feedback to the user as the user brings the fixation device together with the tool, specifically the guide rails of the tool.

An embodiment of the first aspect includes wherein a front leading edge of the sled is curved and a rear trailing edge of the sled is straight and orthogonal to the tab. The benefit of the differing edge conformations is the positive alignment of the sled with rails on the distal tip of the tool.

An embodiment of the first aspect includes wherein a width of the sled is wider than a width of the tissue anchor such that the width of the sled defines a widest-most aspect of the fixation device. The benefit of a wider sled is easy engagement of the sled with the rails on the distal tip of the tool to facilitate loading of the relatively small anchor into the tool.

An embodiment of the first aspect includes wherein the nose comprises: a first barb integrated with the pointed distal end; and a blade integrated with the pointed distal end on an opposing side of the nose opposite from the first barb. The benefit of the conformation of the barb and the pointed end of the anchor is improved tissue penetration, particularly through the relatively tough ligament tissue.

An embodiment of the first aspect includes wherein the nose comprises: a first barb integrated with the pointed distal end; and a second barb located between the first barb and the tail of the tissue anchor. The benefit of two barbs is to ensure strong tissue engagement of the anchor to resist pull-out of the anchor from the tissue.

An embodiment of the first aspect includes having more than one barb and less than three barbs, which facilitates strong tissue engagement with reduced foreign-body size.

An embodiment of the first aspect includes wherein the tissue anchor has an anchor length measured between the pointed distal end and the tail, and a longitudinal length of the tab measured between the distal side and the proximal side of the tab is greater than the anchor length. The benefit of a longer tab compared to the anchor is the improved handling qualities of the fixation device given that the anchor itself is relatively small.

An embodiment of the first aspect includes wherein the tissue anchor has an anchor length measured between the pointed distal end and the tail, and a height of the tab measured between the superior side and the inferior side of the tab is greater than the anchor length. One benefit of a tab being taller than the anchor is the improved handling qualities of the fixation device during a loading of the device into the tool. One benefit of a tab having an area (height and width) as described ensures that the tab is sized to be handled by the finger tips of a surgeon or healthcare worker, even when gloved.

An embodiment of the first aspect includes wherein the tissue anchor has an anchor length measured between the pointed distal end and the tail, and a longitudinal length of the tab and a height of the tab are both greater than the anchor length.

An embodiment of the first aspect includes wherein the tab has a tab width measured between the first face and an opposite second face of the tab, and the first flange projects in the lateral direction away from the first face of the tab by a distance that is greater than the tab width. The benefit of a wide flange compared to the width of the tab is easy of loading the small anchor into the distal tip.

An embodiment of the first aspect includes a break wedge connected between the inferior side of the tab and the tissue anchor, where the break wedge is adapted to allow the tab to be snapped apart from the tail of the tissue anchor. The benefit of a break wedge is a clean removal of the tab from the anchor portion after the anchor is loaded into the distal tip of the tool.

An embodiment of the first aspect includes wherein the break wedge is connected between the inferior side of the tab and the tail of the tissue anchor. The benefit of this location for the break wedge is the leverage it provides to the user when snapping the tab off from the tissue anchor.

An embodiment of the first aspect includes wherein a width of the break wedge measured at a location where the break wedge is connected to the tail is less than a width of the tab and less than a width of the tail. The benefit of this size of a break wedge is to ensure reproducible removal of the tab from the anchor.

A second aspect provides a fixation device comprising:
- a tissue anchor comprising a pointed distal end adapted to penetrate tissue, a barb adapted to engage the tissue, and an eyelet sized to receive a strand of suture; and
- a tab connected to the tissue anchor, with the tab having a distal side opposed to a proximal side and a superior side opposed to an inferior side, and the tab is adapted to be separated from the tissue anchor;
- wherein the tab comprises a sled comprising a first flange coplanar with the inferior side of the tab and projecting in a first lateral direction away from a first face of the tab, and a second flange coplanar with the inferior side of the tab and projecting in a second lateral direction away from a second face of the tab. The advantage of the sled is to locate the relatively small anchor in a properly aligned orientation with the distal tip in a manner that assures proper alignment and prevents skewing the anchor relative to the cannula in the tool. The sled has two flanges that are a haptic feature of the small anchor. The sled is removed when the tab is removed from the anchor.

A third aspect provides a fixation device comprising:
a tissue anchor comprising a distal end adapted to penetrate tissue and a proximal tail end forming an eyelet sized to receive a strand of suture; and
a tab connected to the tissue anchor, with the tab having a first lateral face and an opposing second lateral face; and
a first flange connected to the first lateral face and projecting in a first lateral direction away from the first lateral face. This aspect further comprises a sled connected to the tissue anchor, with the sled comprising the first flange and a second flange, with the second flange connected to the second lateral face and projecting in a second lateral direction away from the second lateral face. This aspect includes the first flange is orthogonal relative to the first lateral face and the second flange is orthogonal relative to the second lateral face.

A fourth aspect provides a tissue anchor system comprising:
a fixation device including a tab connected to a tissue anchor, where the tab includes a sled comprising opposing first and second flanges projecting laterally from opposing first and second faces, respectively, of the tab; and
a tool provided to insert the tissue anchor into tissue, with the tool including a shaft connected between a proximal handle portion and a distal tip;
wherein the distal tip comprises a face extending between a proximal end and a distal end of the distal tip, with a slot formed in the face that is sized to receive the tissue anchor, and a rail projecting away from the face of the distal tip; wherein the rail limits movement of the sled of the fixation device in a distal direction for alignment of the tissue anchor within the slot.

The advantage of the tab is that it provides a handle to allow the user to grasp the relatively small anchor and insert the anchor into the tool.

The advantage of the flange is that it provides a mating index that is useful in aligning the anchor with the cannula of the tool. The flange is a key or an index that mates with a railing on the tool and aligning the flange within the railing of the tool ensures that the relatively small anchor will glide into position within the cannula. Two flanges provide a sled that mates within the rail or railing of the tool.

The railing projects from a surface of the tool and serves to capture the sled, thus locating the tissue anchor in alignment with the cannula of the tool. The railing provides a positive physical feedback informing the user that the sled of the fixation device is properly aligned with the tool. The railing prevents additional proximal displacement (toward the handle of the tool), which informs the user that the fixation device is properly aligned and ready to be pressed downward into the tool for engagement of the fixation device with the cannula of the delivery tool.

An embodiment of the fourth aspect includes wherein the rail comprises a first wall formed on the face of the distal tip and a second wall formed on the face of the distal tip, with the first wall parallel with the distal end of the distal tip. The parallel first wall provides an advantage by acting like a stop feature to prevent movement of the anchor/anchor tab/ anchor sled from moving too far in a distal direction.

An embodiment of the fourth aspect includes wherein the rail comprises a first wall formed on the face of the distal tip and a second wall formed on the face of the distal tip, with the second wall orthogonal to the distal end of the distal tip. The advantage of the second wall is to capture the sled on either side of the distal tip and ensure alignment of the anchor within the slot of the distal tip.

An embodiment of the fourth aspect includes wherein the rail comprises a first wall formed on the face of the distal tip and a second wall formed on the face of the distal tip, with the first wall connected to the second wall.

An embodiment of the fourth aspect includes wherein the rail comprises a first wall formed on the face of the distal tip, with the first wall parallel to the distal end of the distal tip, and a pair of walls orthogonal to the distal end of the distal tip and connected to the first wall, with the first wall and the pair of walls arranged in a U-shape. The U-shape of the rails forms a guide rail that ensures proper alignment of the anchor with the cannula of the tool, even when wearing gloves.

An embodiment of the fourth aspect includes wherein a proximal end of the sled has a sled curvature and the rail projecting from the face of the distal tip has a U-shaped rail curvature, and the U-shaped rail curvature is adapted to mate with the sled curvature. The mating aspect ensures proper alignment of the anchor with the cannula of the tool, even when wearing gloves.

An embodiment of the fourth aspect includes wherein the sled is planar, and co-planar with an inferior side of the tab, such that the sled defines a bottom-most inferior surface of the tab. The sled being co-planar with the bottom of the tab allows tactile feedback when the sled meets with the U-shaped guide rails.

An embodiment of the fourth aspect includes wherein a front leading edge of the sled is curved and a rear trailing edge of the sled is straight and orthogonal to the tab. The advantage of the two different edge shapes provides a visual reminder to the user as to the orientation of the fixation device when preparing the tool for use.

An embodiment of the fourth aspect includes wherein a width of the sled is wider than a width of the tissue anchor such that the width of the sled defines a widest-most aspect of the fixation device. A wide sled provides positive engagement with the distal tip, which is relevant in a surgical suite when wearing gloves.

An embodiment of the fourth aspect includes wherein the tissue anchor comprises a nose having a pointed distal end, with the nose comprising a first barb integrated with the pointed distal end and a blade integrated with the pointed distal end on an opposing side of the nose opposite from the first barb. The pointed distal end provides a visual clue to alignment and use and also penetrates tissue.

An embodiment of the fourth aspect includes wherein the tissue anchor comprises a nose having a pointed distal end, with the nose comprising a first barb integrated with the pointed distal end and a second barb located between the first barb and a tail of the tissue anchor. Two barbs ensure excellent tissue engagement.

An embodiment of the fourth aspect includes wherein the tissue anchor comprises more than one barb and less than three barbs.

An embodiment of the fourth aspect includes wherein the tissue anchor has an anchor length measured between a pointed distal end and a tail of the tissue anchor, and the tab has a longitudinal length measured between a distal side and a proximal side of the tab, and the longitudinal length of the tab is greater than the anchor length. The tab provides a handle for the relatively small tissue anchor, and a large tab is beneficial.

An embodiment of the fourth aspect includes wherein the tissue anchor has an anchor length measured between a pointed distal end and a tail, and the tab has a tab height measured between a superior side and an inferior side of the tab, and the tab height is greater than the anchor length. The benefit is as-above.

An embodiment of the fourth aspect includes wherein the tissue anchor has an anchor length measured between a pointed distal end and a tail, and a longitudinal length of the tab and a height of the tab are both greater than the anchor length.

An embodiment of the fourth aspect includes wherein the tab has a tab width measured between a first face and an opposite second face of the tab, and each flange of the sled projects in a lateral direction away from a respective one of the first face and the opposite second face of the tab by a distance that is greater than the tab width. The tab provides a handle for the relatively small tissue anchor, and a large tab (both height and width) is beneficial, as is a wide sled.

An embodiment of the fourth aspect includes wherein the tab further comprises a break wedge connected between an inferior side of the tab and the tissue anchor, where the break wedge is adapted to allow the tab to be snapped apart from the tissue anchor.

An embodiment of the fourth aspect includes wherein the break wedge is connected between the inferior side of the tab and a tail of the tissue anchor.

An embodiment of the fourth aspect includes wherein a width of the break wedge measured at a location where the break wedge is connected to the tail is less than a width of the tab and less than a width of the tail. The shape and size of the break wedge has the advantage of durability to allow the tab to be used as a handle combined with easy removal of the tab from the anchor.

BRIEF DESCRIPTION OF THE DRAWINGS

The accompanying drawings are included to provide a further understanding of embodiments and are incorporated in and constitute a part of this specification. The drawings illustrate embodiments and together with the description explain principles of embodiments. Other embodiments and advantages of embodiments will be readily appreciated as they become better understood by reference to the following detailed description. The elements of the drawings are not necessarily to scale relative to each other. Like reference numerals designate corresponding similar parts.

FIG. 32C is a side view of the fixation device of FIG. 32B loaded in the distal tip with the tab of the fixation device positioned for removal from the tissue anchor.

FIG. 32D is a side view of the fixation device of FIG. 32C with the tab of the fixation device rotated prior to complete removal of the tab from the tissue anchor.

FIG. 32E is a side view of the fixation device of FIG. 32B with a sled of the fixation device located too far distal and improperly positioned for removal of the tab from the fixation device.

FIG. 32F is a side view of the tab of the fixation device completely removed from the tissue anchor with the tissue anchor retained in the distal tip of the delivery device.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used regarding the orientation of the Figure(s) being described. Because components of embodiments can be positioned in several different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The features of the various exemplary embodiments described in this application may be combined with each other, unless specifically noted otherwise. The term "proximal" in this application means that part that is situated next to or near the point of attachment or origin or a central point; for example, as located toward a center of the human body. The portion of an implant that is closest to a center of a patient's body is the proximal portion of the implant, whereas for a surgical tool having a handle and a working head, the handle held by the surgeon is a proximal portion of the tool.

The term "distal" in this application means that part that is situated away from the point of attachment or origin or the central point; for example, as located away from the center of the human body. The working head of the surgical tool is distal relative to the proximal handle.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12-inch ruler has a center at 6 inches, a first end at zero inches and a second, opposite end at 12 inches, a first end portion adjacent to the first end and a second end portion adjacent to the second end.

Figure 1:
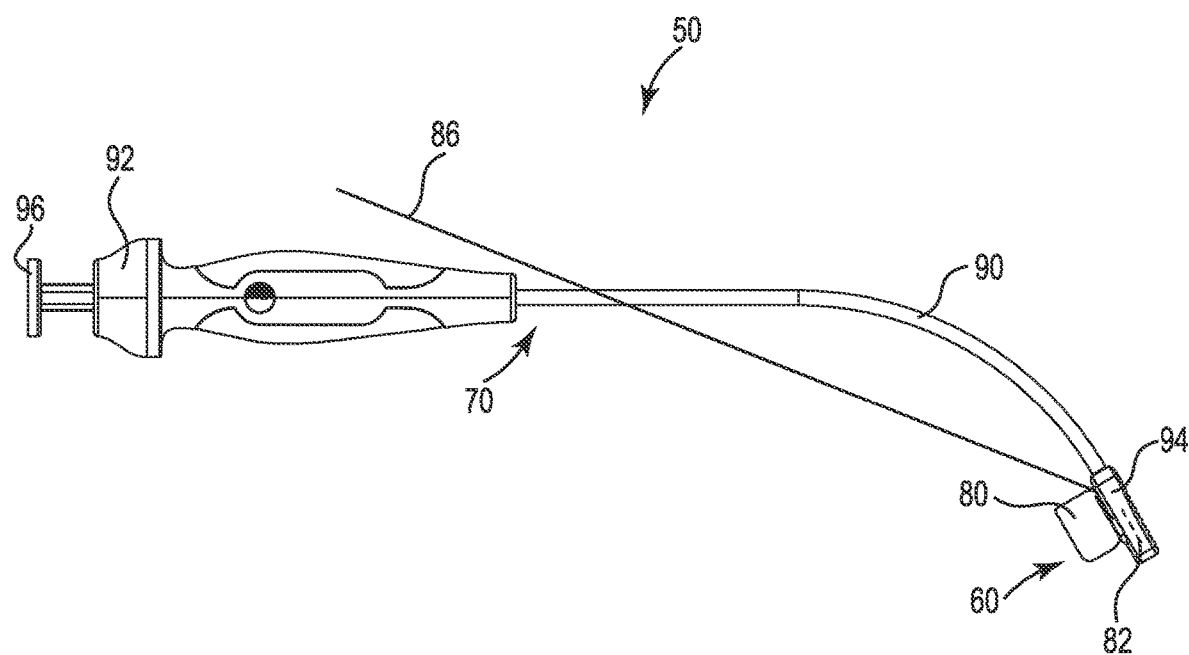
FIG. 1 is a front view of one embodiment of a tissue anchor system including a tissue fixation device inserted into a delivery tool.

FIG. 1 is a front view of one embodiment of a tissue anchor system 50 including a tissue fixation device 60 inserted into a delivery device 70. The system 50 allows transvaginal implantation of tissue fixation anchors, which serve as fixation points for suture attachment during pelvic reconstruction in the treatment of pelvic organ prolapse.

The system 50 includes a single-use tissue fixation anchor delivery device 70 and one or more, and in some embodiments a pack of several, shelf-stable tissue fixation devices 60.

The system 50 allows the surgeon to choose most off-the-shelf sutures (which are not included with the system). Each of the tissue fixation devices 60 include an eyelet formed in each anchor, where the eyelet is benfically sized to receive up to two USP (United States Pharmacopeia) size 0 or smaller sutures and any needles coupled to a suture.

The tissue fixation device 60 includes a tab 80 connected to a tissue anchor 82. The tissue anchor 82 (or anchor 82, See FIG. 2) is not visible in FIG. 1 because the anchor 82 has been loaded into the delivery tool 70. The tab 80 is configured to be separated from the anchor 82 after loading of the anchor 82 into the tool 70 and prior to placement of the anchor 82 into tissue. Thus, the view of FIG. 1 is immediately prior to removal of the tab 80 during the surgical procedure.

The anchor 82 is configured to allow the surgeon to select whichever form of suture is desired for the specific patient and procedure, and then pass that suture through an eyelet of the anchor 82. The surgeon at times may desire two or more suture lines to be threaded through the anchor 82, and some of the suture might have a needle secured at one end. Generally, it is difficult to pass even one-such suture line through a conventional tissue anchor because conventional eyelets are small and sized to receive one line of suture. In contrast, the anchor 82 is adapted to receive and engage with multiple such suture lines. The anchor 82 is compatible with all known forms of suture 86, including resorbable suture, bioabsorbable suture, biodegradable suture, and non-resorbable suture.

The delivery device 70 (or tool 70) has a shaft 90 connected between a proximal handle 92 and a distal tip 94, where the proximal handle 92 includes a plunger 96 for moving/pushing the anchor 82 out of the distal tip 94.

The delivery device 70/tool 70 is made of polycarbonate/ABS (acrylonitrile butadiene styrene) for the handle 92 and the plunger 96; a stainless-steel shaft 90 that forms the cannula inside of the distal tip 96, where the distal tip is fabricated from a polyurethane.

The fixation device 60 is suitably fabricated from plastic or metal. Exemplary tissue fixation devices 60 (tab 80 and anchor 82) are suitably fabricated from a polymer, such as polysulfone or polyether-ether-ketone. The system 50 is provided sterile (gamma radiation sterilized is one acceptable method) and is for single patient use only. Other suitable sterilization techniques for sterilizing the fixation devices 60 and the delivery tool 70 are also acceptable.

The tissue anchor system 50 provides a single-use device that allows the surgeon to place the anchor(s) 82 into muscles or ligaments in the pelvic floor to support prolapsed pelvic organs. The system 50 is useful in procedures such as sacrospinous ligament fixation and augmentation repairs of the anterior or posterior compartments, which, depending upon the surgeon's preference, may include synthetic mesh or biologic grafts. The anchor 82 is compatible with various commercially available sutures, including sutures without needles, suture with one needle, and those that are double armed with needles. The tool 70, while disposable, is reloadable with subsequent anchors 82 for placement of several anchors into the patient during a fixation or augmentation procedure.

Figure 2:
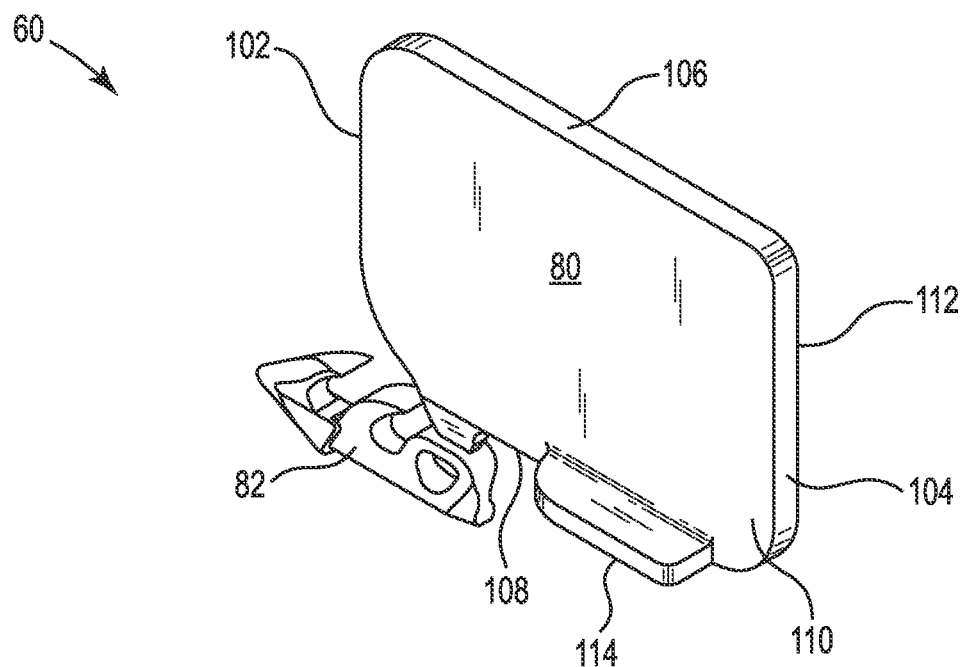
FIG. 2 is a perspective view of one embodiment of the tissue fixation device including a tab connected to a tissue anchor.

FIG. 2 is a perspective view of one embodiment of the tissue fixation device 60 including the tab 80 connected to the tissue anchor 82 (anchor 82). The tab 80 is large relative to the anchor 82 and has a distal side 102 opposed to a proximal side 104 and a superior side 106 opposed to an inferior side 108. The tab 80 is generally rectangular and includes a first face 110 opposite from a second face 112, although other shapes are acceptable. The tab 80 has a first flange 114 connected to the inferior side 108, where the first flange 110 projects in a lateral direction away from the first face 110 of the tab 80. The flange 114 is provided to steady and guide the engagement of the fixation device 60 with the tool 70 (FIG. 1). In one embodiment, the fixation device 60 acceptably includes a single (one-and-only-one) flange 114 that is co-planar with the inferior side 108 of the tab 80. Alternatively, a second flange 115 (FIG. 4 and FIG. 5) is provided that projects in a lateral direction away from the second face 112 of the tab 80, where the two flanges (when so provided) combine to form a sled 116 (FIG. 5). The tab 80 is adapted to be separated from the tissue anchor 82.

Figure 3:
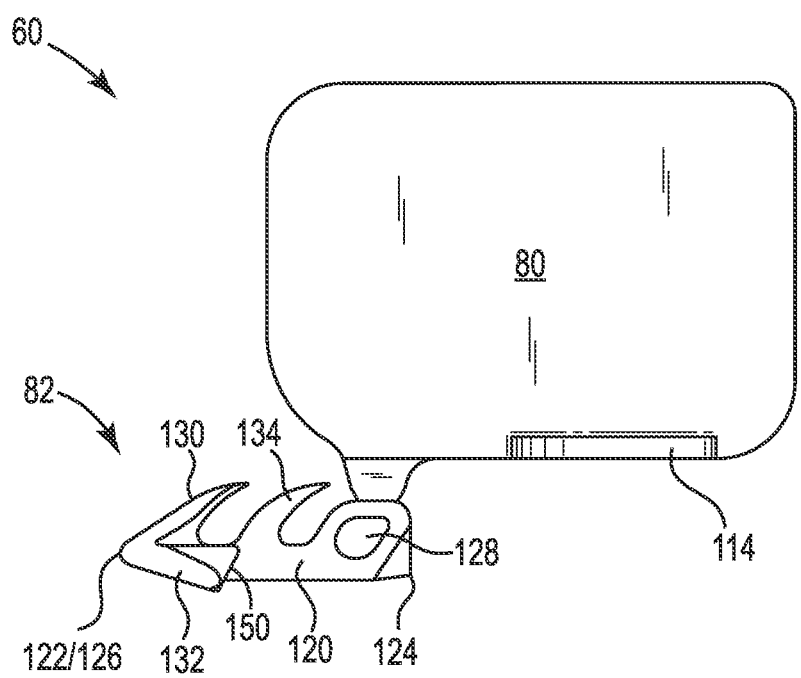
FIG. 3 is a front view of the tissue fixation device relative to the orientation of the tissue fixation device shown in FIG. 2.
Figure 4:
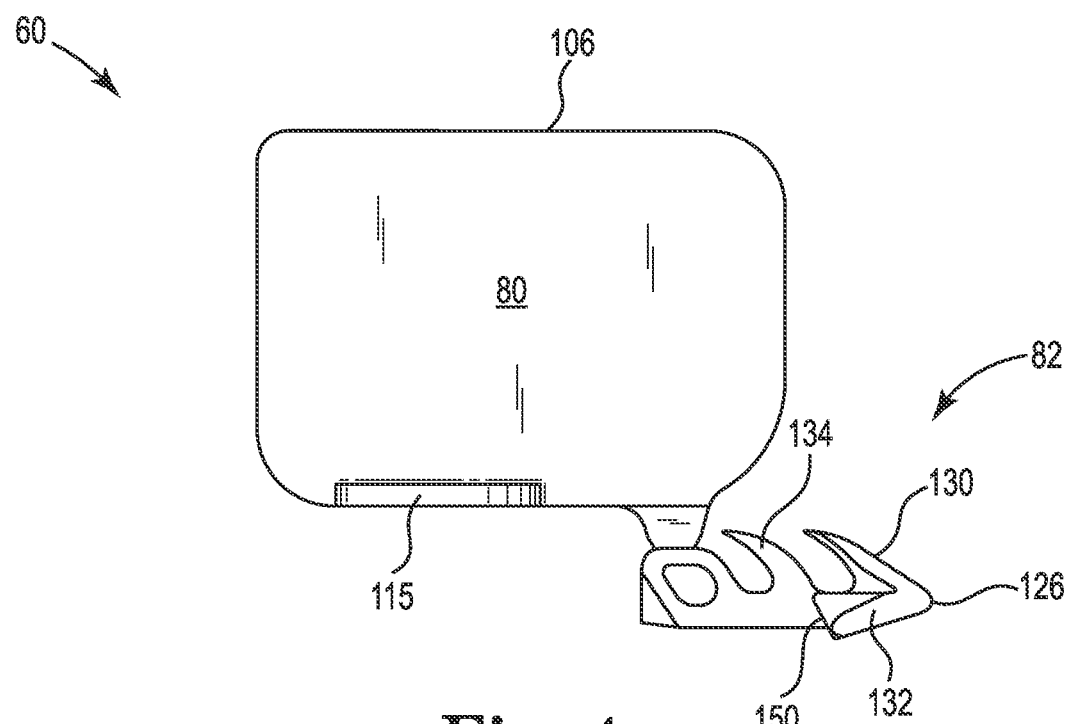
FIG. 4 is a back view of the tissue fixation device relative to the orientation of the tissue fixation device shown in FIG. 2.
Figure 5:
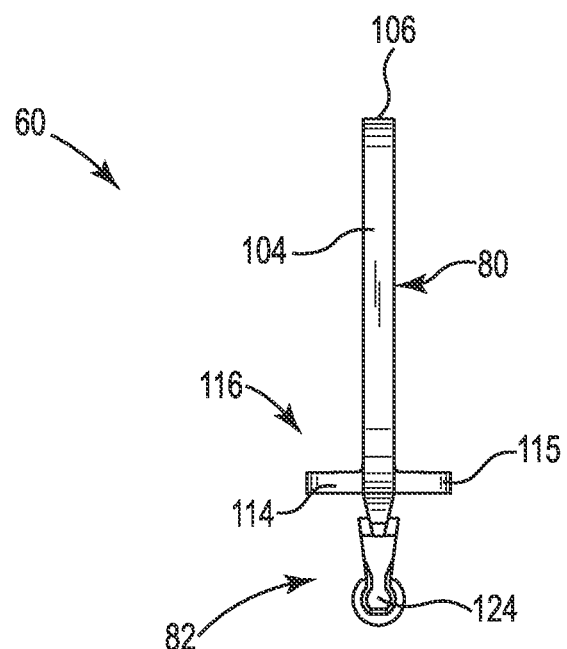
FIG. 5 is a left side view of the tissue fixation device relative to the orientation of the tissue fixation device shown in FIG. 2 (i.e., looking at the back or proximal end of the anchor).

FIG. 3 is a front view and FIG. 4 is a back view (relative to the perspective view of FIG. 2) of the tissue fixation device 60. The anchor 82 has a body 120 extending longitudinally between a nose 122 and a tail 124 of the anchor, with the nose 122 having a pointed distal end 126 adapted to pierce and penetrate tissue and the tail forming an eyelet 128 sized to receive at least two strands of suture and any needle(s) coupled to suture(s).

The nose 122 has a first barb 130 integrated to extend contiguously from the pointed distal end 126, and a blade 132 integrated with the pointed distal end. The blade 132 is present on both opposing sides of the nose 122 and inferior to, or opposite from, the first barb 130. The first barb 130 is provided to engage with tissue after the pointed end 126 and the blade 132 have parted the tissue. The illustrated embodiment includes a second barb 134 located between the first barb 130 and the tail 124 of the anchor 82, although one barb 130 or several barbs are acceptable.

The back side view of FIG. 4 illustrates the second flange 115, which in combination with the first flange 114 (FIG. 3), provides the guidance or alignment sled 116 referenced above.

The tab 80 is about 12 mm tall, about 18 mm wide, and about 0.6 mm thick. Each flange 114, 115 of the tab 80 extends about 2 mm from its respective face. In combination, the two flanges form the sled 116, which is about 6.6 mm long and about 4.6 mm wide, and each flange 114, 115 has a thickness of about 0.7 mm. The longitudinal length of the anchor 82 is about 9.3 mm between the end 126 and the tail 124, with the portion of the tail 124 that forms the eyelet having a length of about 3 mm. The length of the fixation device from the distal end 126 of the anchor 82 to the proximal side 104 of the tab 80 is about 21.5 mm. The eyelet 128 is a form of an asymmetric ellipse having a long axis of about 1.7 mm and a short axis of about 1.3 mm, which provides an eyelet having a generally large area of more than 2 square mm. The smaller corner of the eyelet 128 is positioned so that when under traction, the suture 86 will shift to the smaller corner and pull the anchor 82 along a line of tension that passes through the middle of the barbs. This optimizes and increases the stability and holding strength of the anchor in tissue. The large area of the eyelet 128 allows two or more double-ended sutures to pass through the anchor 82.

FIG. 3 and FIG. 4 show the blade 132 terminates at a shoulder 150, and the shoulder 150 is disposed at an angle of about 118 degrees from the longitudinal axis that extends horizontally from the tail 124 through the end 126. The first barb 130 extends contiguously from the pointed distal end 126 and is elevated above the longitudinal axis at an angle of about 25 degrees. The first barb 130 and the blade 132 form an arrow shape having an approximately 50 degree included angle. The dimensions above have proven to engage well with sacrospinous and other pelvic tissue, although other suitable dimensions would be acceptable.

Figure 6:
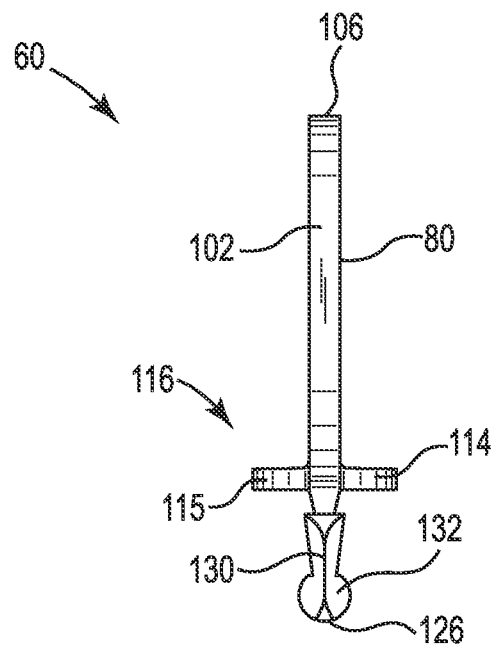
FIG. 6 is a right side view of the tissue fixation device relative to the orientation of the tissue fixation device shown in FIG. 2 (i.e., looking at the point at the front or distal end of the anchor).
Figure 7:
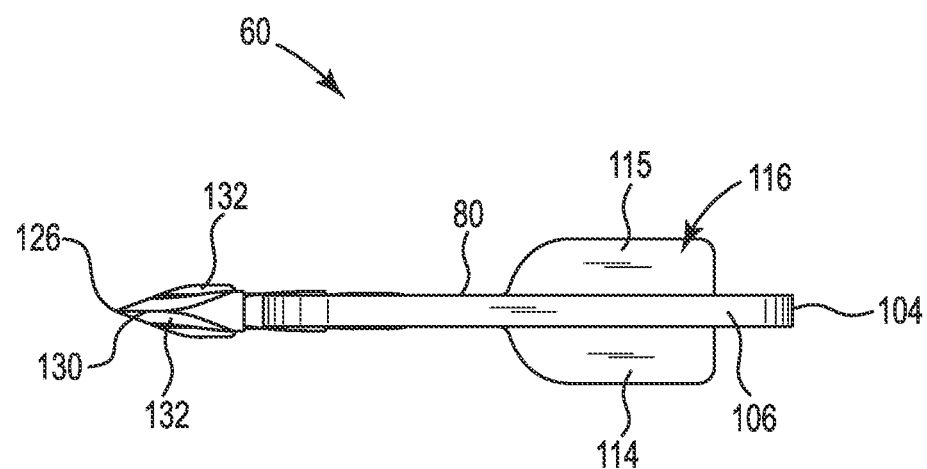
FIG. 7 is a top view of the tissue fixation device relative to the orientation of the tissue fixation device shown in FIG. 2.
Figure 8:
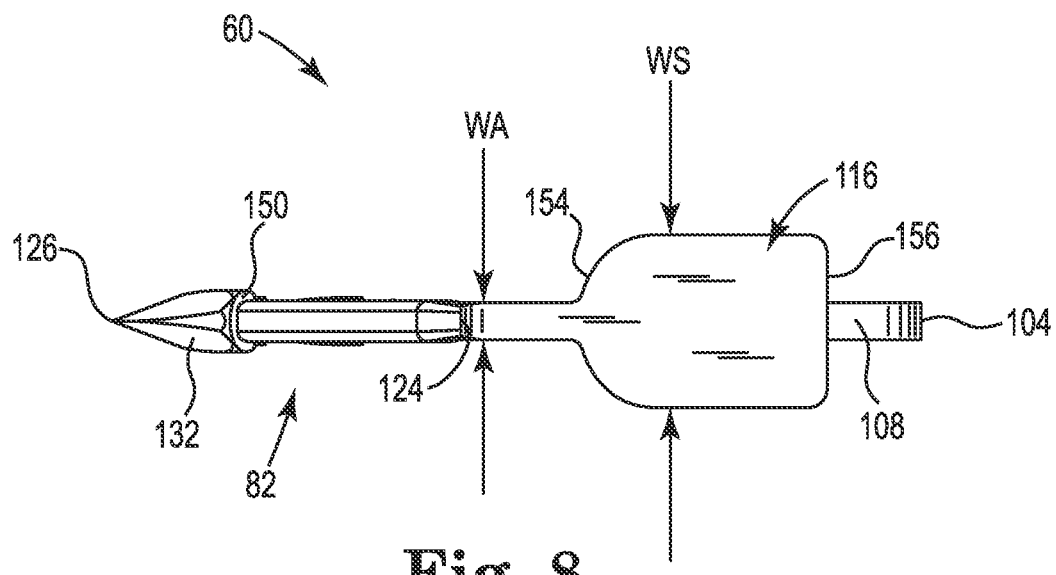
FIG. 8 is a bottom view of the tissue fixation device relative to the orientation of the tissue fixation device shown in FIG. 2.

FIG. 5 is a right side view (i.e., the back of the anchor), FIG. 6 is a left side view (i.e., the front of the anchor), FIG. 7 is a top view, and FIG. 8 is a bottom view (relative to the perspective view of FIG. 2) of the tissue fixation device 60 illustrating the relationship of the tab 80 and the sled 116 relative to the anchor 82.

With reference to FIG. 2 through FIG. 5, the tissue anchor 82 has an anchor length measured between a pointed distal end 122/126 and the tail 128, and the tab 80 has a longitudinal length measured between a distal side 102 and a proximal side 104, and the longitudinal length of the tab is greater than the anchor length. The tab 80 has a tab height measured between the superior side 106 and the inferior side 108, and the tab height is greater than the anchor length; and the longitudinal length of the tab and the height of the tab are both greater than the anchor length. The tab has a tab width measured between the first face 110 and an opposite second face 112, and the first flange 114 projects in the lateral direction away from the first face 110 of the tab by a distance that is greater than the tab width.

Referring to FIG. 8, the sled 116 is planar and is co-planar with the tab 80 to define a bottom-most inferior surface of the tab 80. The front leading edge 154 of the sled 116 is curved and a rear trailing edge 156 of the sled 116 is straight and orthogonal to the tab 80. A width WS of the sled 116 is wider than a width WA of the tissue anchor 82 such that the width of the sled 116 defines a widest-most aspect of the fixation device 60.

Figures 9A, 9B:
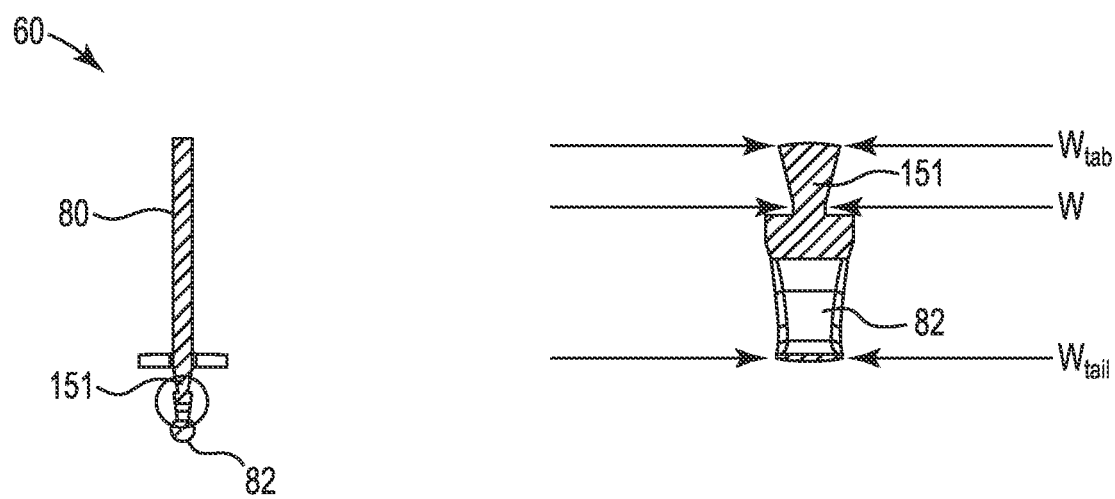
FIG. 9A is a cross-sectional view of a location of attachment between the tab and the tissue anchor for the tissue fixation device.
FIG. 9B is an enlarged view taken of FIG. 9A.

FIG. 9A and FIG. 9B are a cross-sectional views of the location of attachment between the tab 80 and the anchor 82. The tab 80 is configured to break off from and to separate from the anchor 80, and in one embodiment includes a break wedge 151 connected between the inferior side 108 of the tab 80 and the anchor 82. The break wedge 151 tapers in thickness from the tab 80 down to the connection edge at the tail 124. The break wedge 151 is adapted to allow the tab 80 to be snapped apart from the tail 124 of the anchor 82. One embodiment of the break wedge 151 includes a width W of the break wedge 151, when measured at a location where the break wedge 151 is connected to the tail 124, being less than a width Wtab of the tab 80 and less than a width Wtail of the tail 124. The narrower width W of the break wedge 151 allows the tab 80 to snap cleanly away from the anchor 82.

With reference to FIG. 1 and FIG. 3, the system 50 is useful for placing anchors into tissue of the pelvis in the treatment of organ prolapse, and one such operation includes the following steps. The fixation device 60 will be removed from its package. The surgeon will select one or more sutures 86, and the suture 86 will be inserted into the eyelet 128 of the fixation device 60. The fixation device 60 will be held by the tab 80 and loaded into the distal tip 94 of the delivery tool 70 by mating the flange 114, or the sled 116 if so provided, to a railing or guide on the distal tip 94 of the tool 70. When the fixation device 60 is aligned with the distal tip 94, the fixation device 60 is moved in a proximal direction (e.g., rearward toward the handle 92) and the anchor 82 is retained within the distal tip 94. The tab 80 will be removed from the fixation device 60, leaving the tissue anchor 82 and the suture 86 in the distal tip 94 of the tool 70. A retention device (various embodiments are described below) maintains the anchor 82 within the distal tip 94 as the distal tip 94 of the tool 70 is passed transvaginally to a target tissue within the pelvis. The surgeon will guide the distal tip 94 of the tool 70 with finger(s) of one hand while holding the handle 92 of the tool 70 with the other hand, which allows the surgeon to palpate the target landmark with his/her fingers. The distal tip 94 will be positioned against the target landmark and the surgeon will eject the tissue anchor 82 and the suture 90 out of the distal tip 94 by pressing the plunger 96, which passes the tissue anchor 82 into the target tissue. The tool 70 may then be removed from the patient and reloaded with another anchor 82 and suture(s) 86, if desired by the surgeon.

Figure 10A:
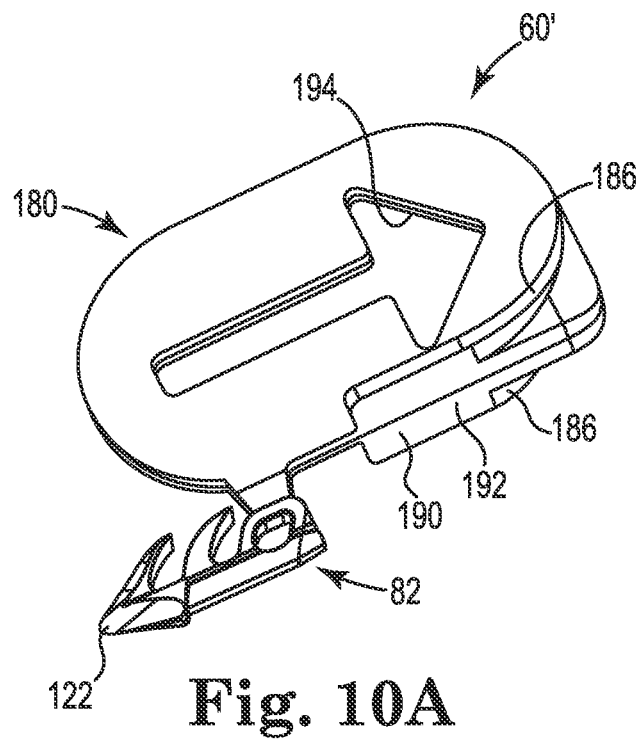
FIG. 10A is a perspective view of one embodiment of a tissue fixation device including a tab connected to a tissue anchor.

FIG. 10A is a perspective view of one embodiment of a tissue fixation device 60' including a tab 180 removably connected to the anchor 82. The tab 180 has a curved-flanged sled 186, where the curvature of the sled 186 curves from a base 190 of the sled 186 in a proximal direction. The sled 186 has a section 192 of a planar and flat base and the curved-flanged portion 186. The curved-flanged sled 186 allows the healthcare worked to rock the fixation device 60' with the anchor tip 122 elevated for an improved view into the slot in the distal tip 94 (FIG. 1). Once aligned, the fixation device 60' is rocked to a level orientation with the distal tip 94, and the anchor 82 is loaded. Note that the tab 180 includes an orientation indicium, which in this embodiment is a direction arrow 194 formed or punched through the tab 180. The tab 180 is subsequently removed and discarded after the anchor 82 is loaded into the distal tip 94.

Figure 10B:
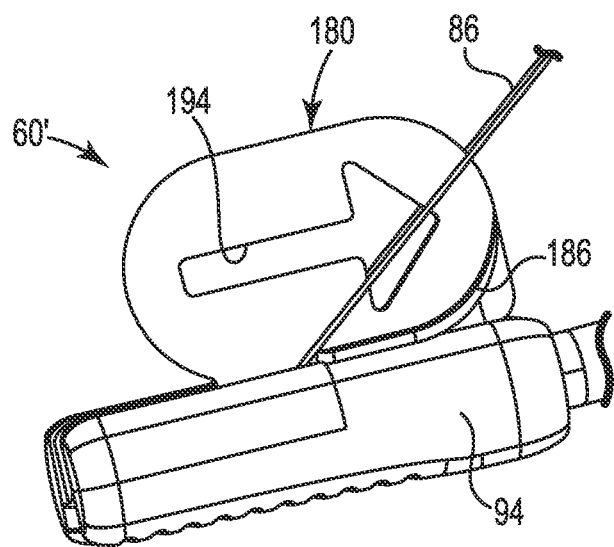
FIG. 10B is a side view of the tissue fixation device of FIG. 10A inserted into a distal tip of the delivery device shown in FIG. 1.

FIG. 10B is a side view of the tissue fixation device 60' engaged with a distal tip 94. The curved sled 186 allows the fixation device 60' to be rocked into engagement and offers a direct line of sight view of the anchor 82 as it engages with the distal tip 94.

Figure 11:
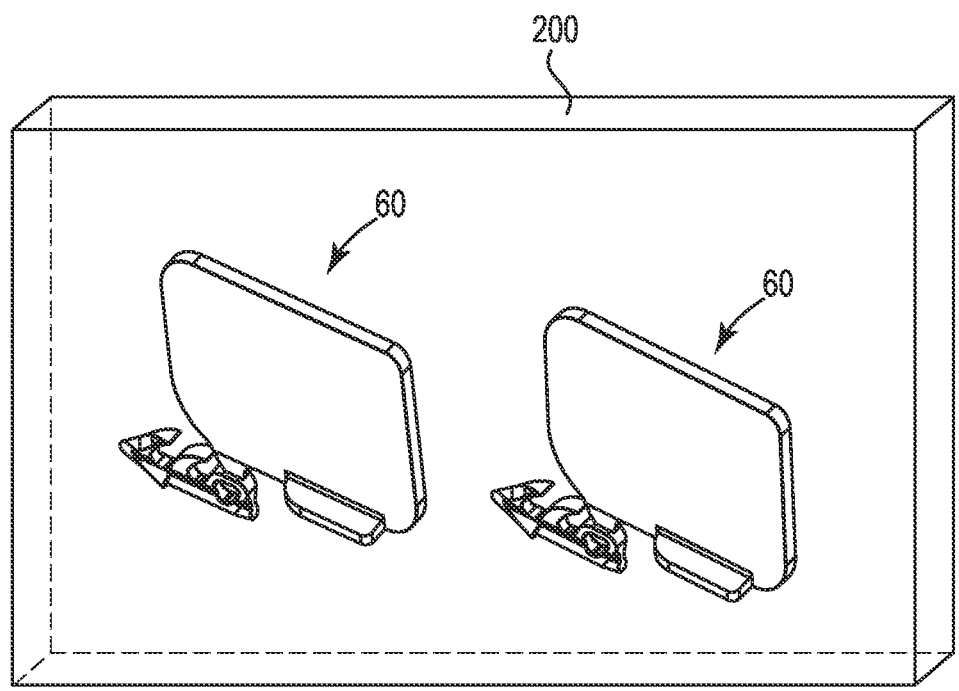
FIG. 11 is a perspective view of a kit of parts including a plurality of tissue fixation devices contained in a package.

FIG. 11 is a perspective view of a plurality of fixation devices 60 packaged in a kit 200 or package 200. Two fixation devices 60 are illustrated, but more than two fixation devices may be provided in the kit 200. During some pelvic floor repair procedures, the surgeon might desire to have more fixation devices 60 on hand, and the package 200 of additional devices 60 allows the surgeon to have this flexibility.

Figure 12:
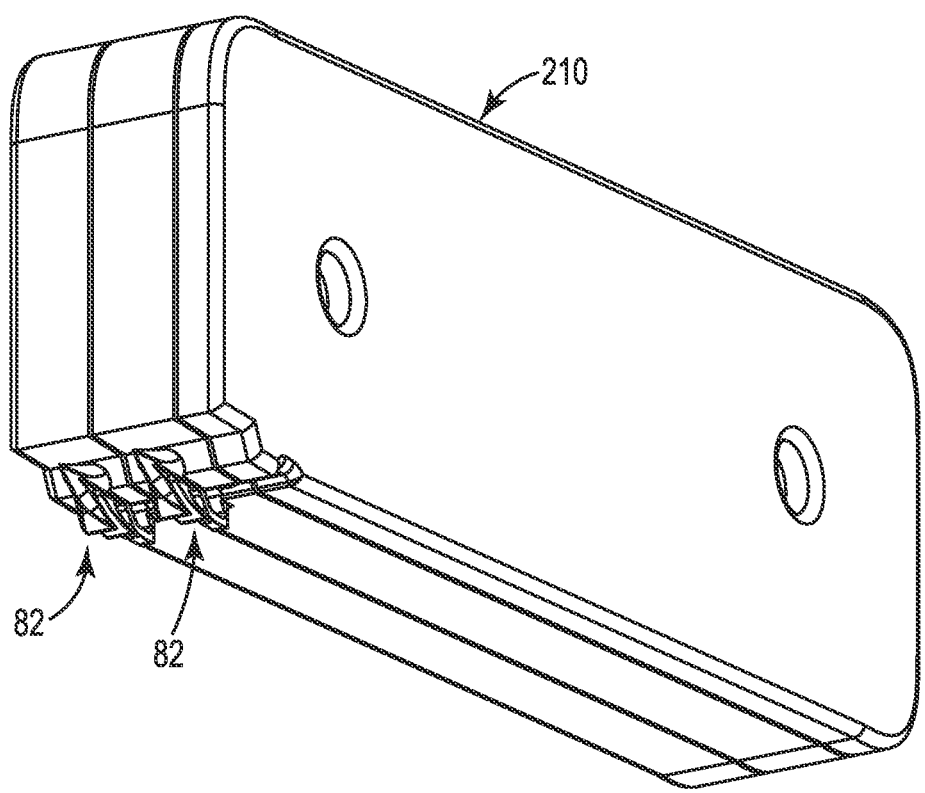
FIG. 12 is a perspective view of one embodiment of cartridge maintaining a plurality of tissue fixation devices.

FIG. 12 is a perspective view of one embodiment of a cartridge 210 adapted to hold a plurality of tissue anchors 82. Some surgeons have expressed a desire to have a cartridge that facilitates loading of the small anchors 82 into the tool 70, and the cartridge in this embodiment holds two such anchors for eventual loading into the tool 70.

Figure 13:
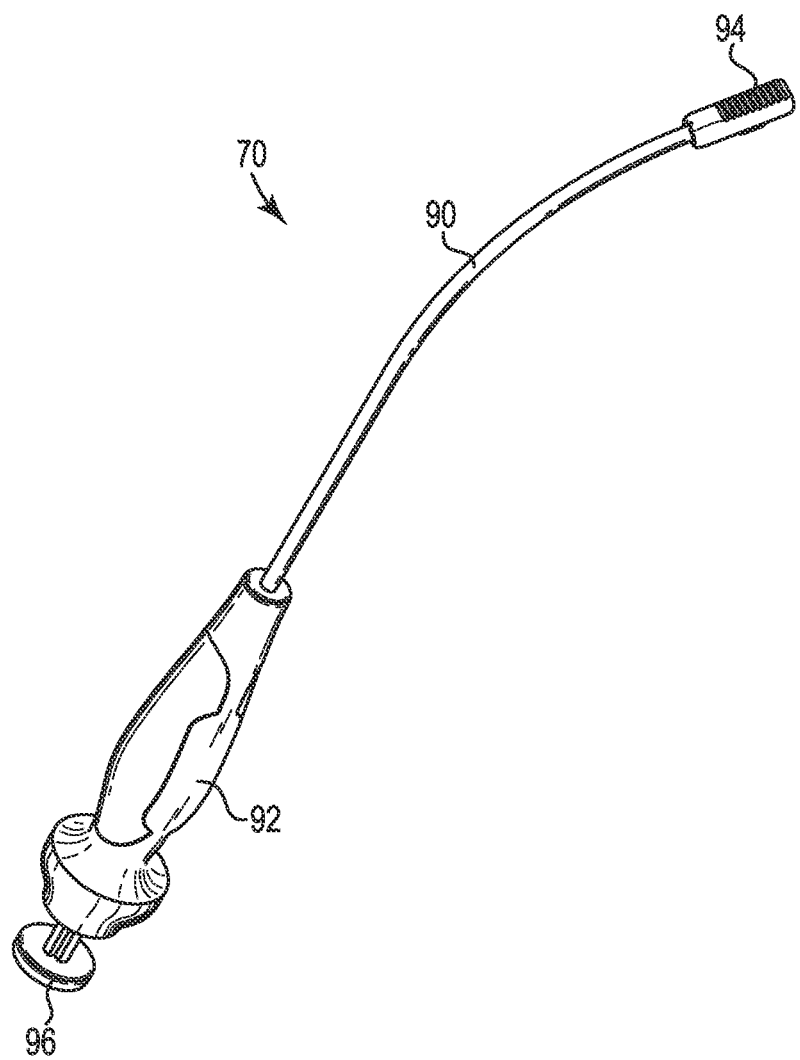
FIG. 13 is a perspective view of one embodiment of the delivery tool (tool) of the tissue anchor system.
Figure 14:
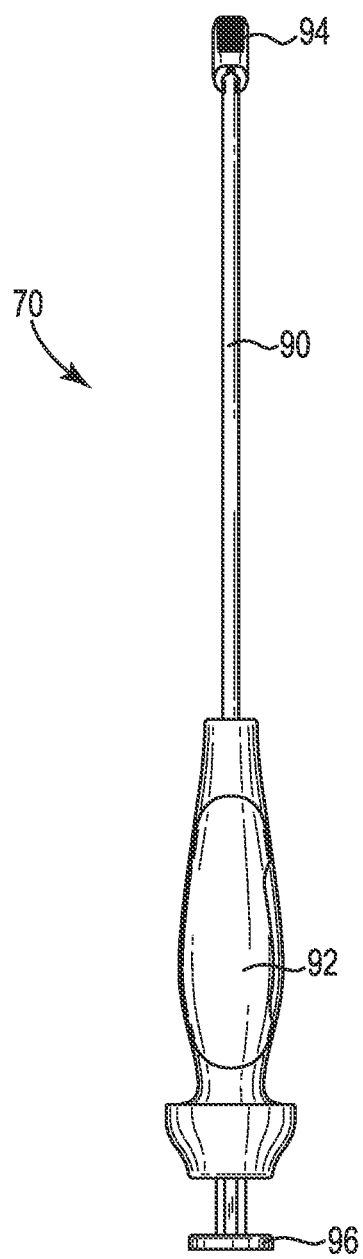
FIG. 14 is a top view of the tool.

FIG. 13 is a front view and FIG. 14 is a top view of one embodiment of the delivery tool 70 (or tool 70). The tool 70 includes the handle 92 having the plunger 96 on a proximal end of the tool 70, with the handle 92 connected to the shaft 90 and the plunger 96 communicating with through a cannula or lumen inside of the shaft 90, with the shaft 90 connected to the distal tip 94 of the tool 70.

Figure 15:
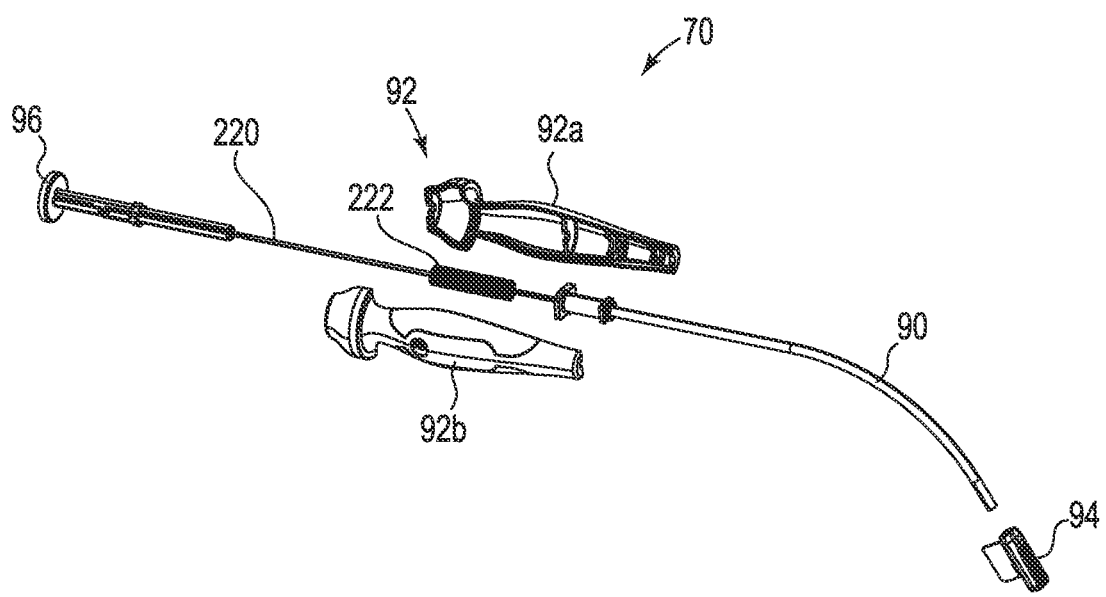
FIG. 15 is an exploded view of the tool.

FIG. 15 is an exploded view of the tool 70. The handle 92 encloses a cannula drive shaft 220 and a return spring 222, where the cannula drive shaft 220 is configured to push a loaded anchor out of the distal tip 94 when the plunger 96 is pushed in the distal direction. The return spring 222 biases the plunger 96 and operates to return the plunger 96 to its initial position. In this exemplary embodiment, the handle 92 is a two-piece mated shell that includes a left 92a handle section and a right 92b handle section that mate together to capture the plunger 96 and enclose the cannula drive shaft 220 and the return spring 222.

Figure 16:
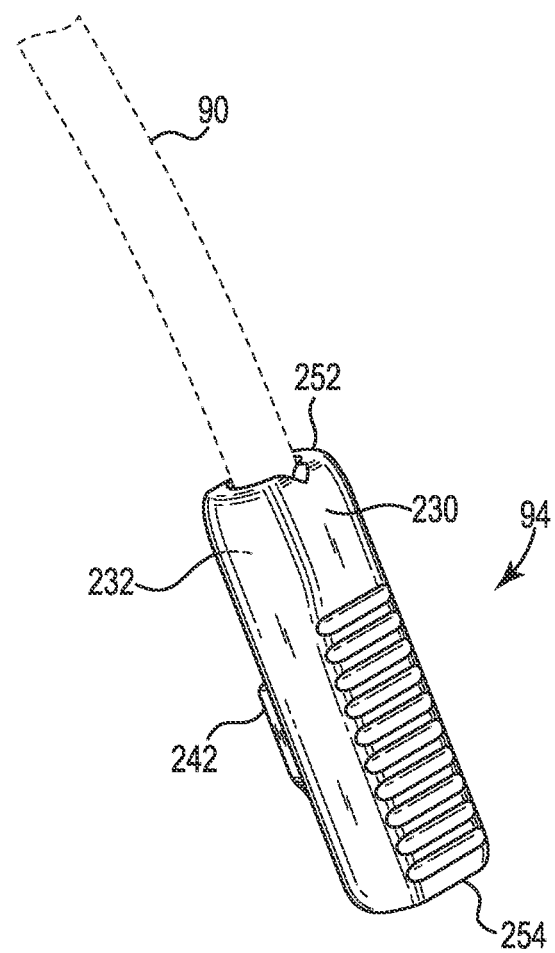
FIG. 16 is a perspective view of one embodiment of a distal tip of the tool.
Figure 17:
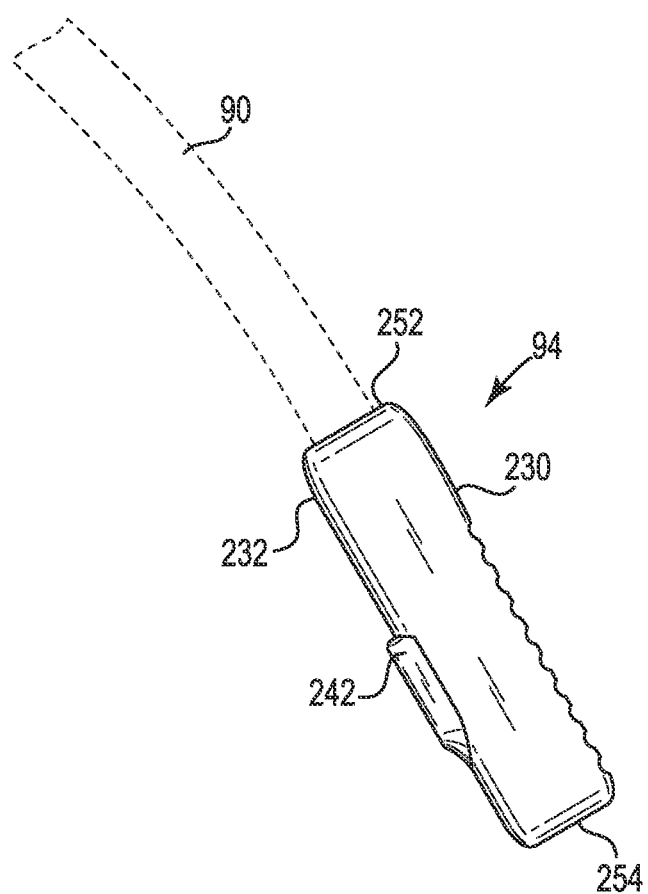
FIG. 17 is a front view of the distal tip relative to the orientation of the distal tip shown in FIG. 16.
Figure 18:
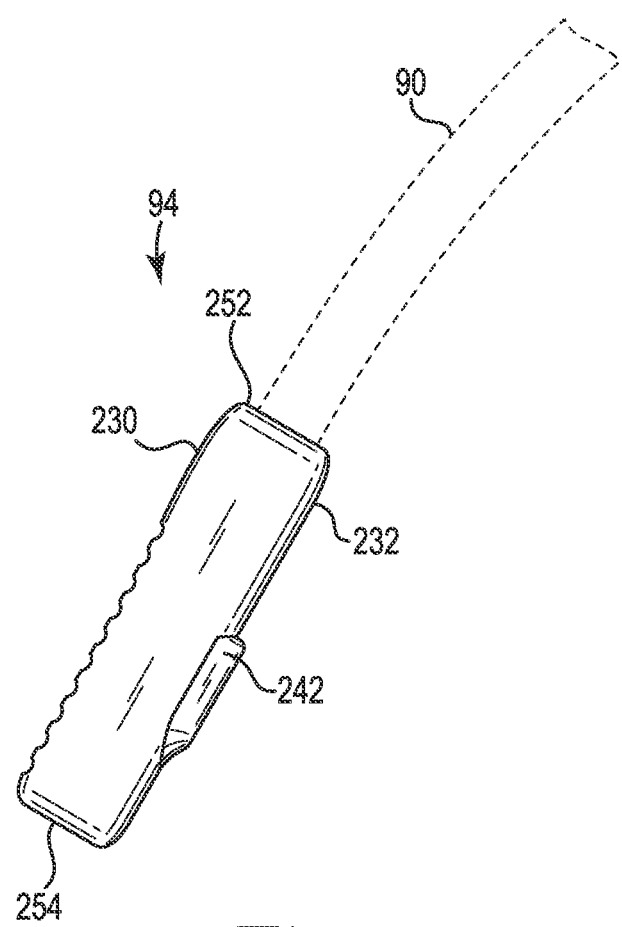
FIG. 18 is a back view of the distal tip relative to the orientation of the distal tip shown in FIG. 16.
Figure 19:
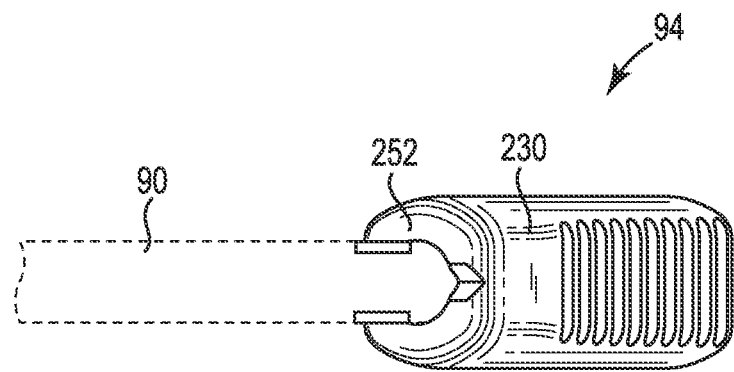
FIG. 19 is a right side view of a distal end of the distal tip relative to the orientation of the distal tip shown in FIG. 16 (e.g., a top view of the distal tip).
Figure 20:
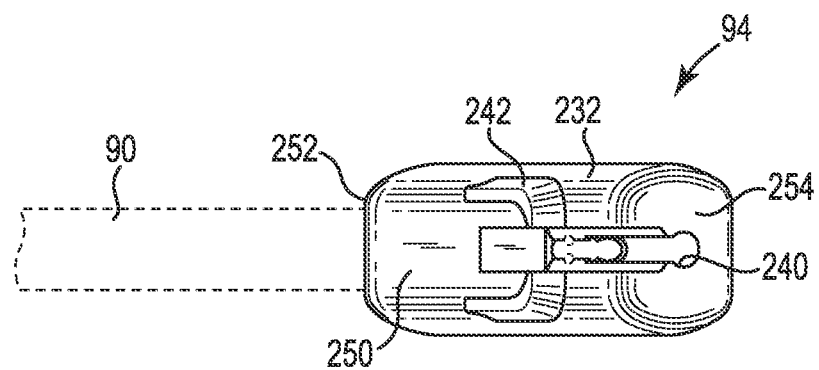
FIG. 20 is a left side view of a proximal end of the distal tip relative to the orientation of the distal tip shown in FIG. 16 (e.g., a bottom view of the distal tip).

FIG. 16 is a perspective view, FIG. 17 is a front view, FIG. 18 is a back view, FIG. 19 is a right side view, and FIG. 20 is a left side view of one embodiment of the distal tip 94. The distal tip 94 includes a superior side 230 opposite from an inferior side 232, a slot 240 formed in the inferior side 232, and a guide rail 242 (or rail 242) projecting from the inferior side 232 of the distal tip 94. The superior side of the distal tip 94 includes a corrugated or ribbed surface that both aids the surgeon in determining the orientation of the distal tip 94 and provides a no-slip surface.

The inferior side 232 of the distal tip 94 includes a face 250 extending between a proximal end 252 and a distal end 254, with the slot 240 formed in the face 250 and sized to receive the tissue anchor 82. The rail 242 projects away from the face 250 of the distal tip 208.

Figure 21:
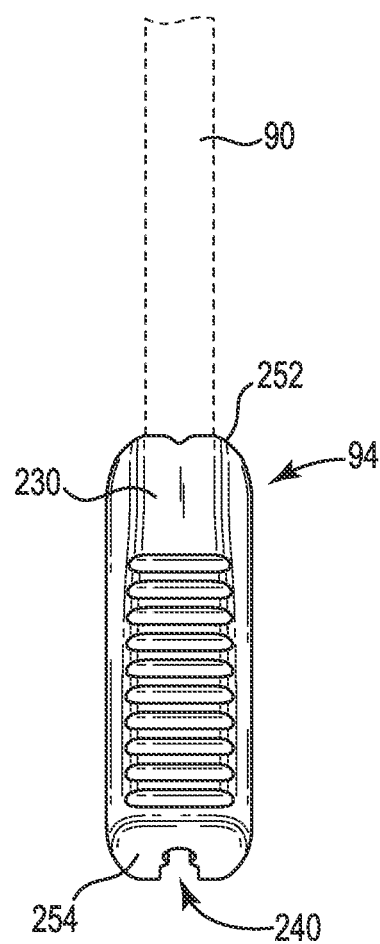
FIG. 21 is a top view of the distal tip (e.g., a right side view of the distal tip).
Figure 22:
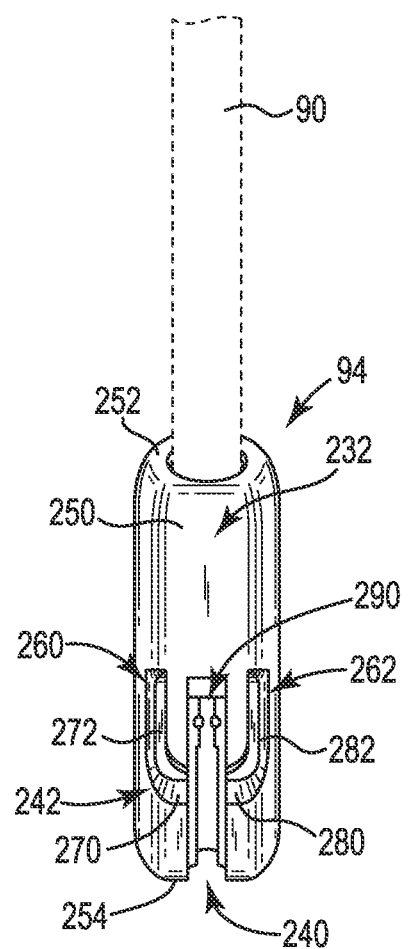
FIG. 22 is a bottom view of the distal tip (e.g., a left side view of the distal tip).

FIG. 21 is a view of the superior side 230 and FIG. 22 is a view of the inferior side 232 of the distal tip 94. The fixation device 60 (FIG. 2) is loaded into the slot 240 formed in the inferior side 232 of the distal tip 94 and the orientation and proper alignment of the fixation device 60 with the slot 240 is aided by the guide rail 242 projecting away from the inferior side 232 of the distal tip 94.

The face 250 of the inferior side 232 extends between the ends 252, 254 and the rail 242 projects away from the face 250 to provide a haptic engagement ridge that helps align the anchor 82 with the slot 240. The shaft 90 of the tool 70 is inserted into the proximal end 252 of the distal tip 94.

Referring to FIG. 22, the rail 242 limits movement of the sled 116 (FIG. 5 and FIG. 8) of the fixation device 60 in the distal direction (toward the distal end 254), which serves to properly align of the tissue anchor 82 within the slot 240. The rail 242 has a portion located on each side of the slot 240.

The rail 242 has a first portion 260 on a first side of the slot 240 and a second portion 262 on a second, opposing side of the slot 240. The first portion 260 of the rail 242 has a first wall 270 connecting with a second wall 272, with both walls 270, 272 formed to project away from the face 250 of the distal tip 208. The first wall 270 parallel with the distal end 254 of the distal tip 94, and the second wall 272 is orthogonal to the distal end 254 of the distal tip 208 and is parallel with a side of the distal tip 94 and parallel with a portion of the slot 240.

The second portion 262 of the rail 242 likewise has a first wall 280 parallel with the distal end 254 of the distal tip 94, and a second wall 282 orthogonal to the distal end 254 of the distal tip 94 and connected to the first wall 280. In combination around the slot 240, the walls 270, 272 and the walls 280, 282 form a U-shaped guide rail 242 that is adapted to mate or secure the sled 116 of the tissue fixation device 60 so the anchor 82 is in proper alignment with the slot 240.

With reference to FIG. 5 and FIG. 22, after the proper alignment of the anchor 82 is achieved relative to the slot 240, the healthcare worker pulls the tab 80 in a proximal direction to seat the anchor 82 into an anchor retention device provided by the distal tip 94. The anchor 82 positively engages with the retention device, the action of which can be felt or heard or both, and this indicates to the healthcare worker that the tab 80 is ready to be separated from the anchor 82.

FIG. 22 is a view into the slot 240 looking at the inferior side 232 of the distal tip 94. An anchor retention device 290 is formed inside of the slot 226. In one embodiment, the anchor retention device 290 is formed as opposing projections that frictionally engage with the eyelet 128 of the anchor 82 (See FIG. 2). The opposing projections of the anchor retention device 290 include a first projection on a first side of the slot and a second projection on a second side of the slot, with a gap distance separating the first and second projections. The anchor 82 is sized to slide between and force apart the first and second projections, and with additional movement of the anchor 82 in the proximal direction into the slot 240, the first and second projections enter and engage the eyelet 128 of the anchor 82. The tab 80 is employed as a handle to pull the fixation device 60 in a proximal direction toward the handle 92, which ensures that the anchor 82 seats within the anchor retention device 290.

With reference to FIG. 8 and FIG. 22, the proximal end 154 of the sled 116 has a sled curvature and the rail 242 projecting from the face of the distal tip 94 has a rail curvature formed by the U-shape rails 270, 272 and 280, 282, and the rail curvature is adapted to mate with the sled curvature 154.

Figure 23:
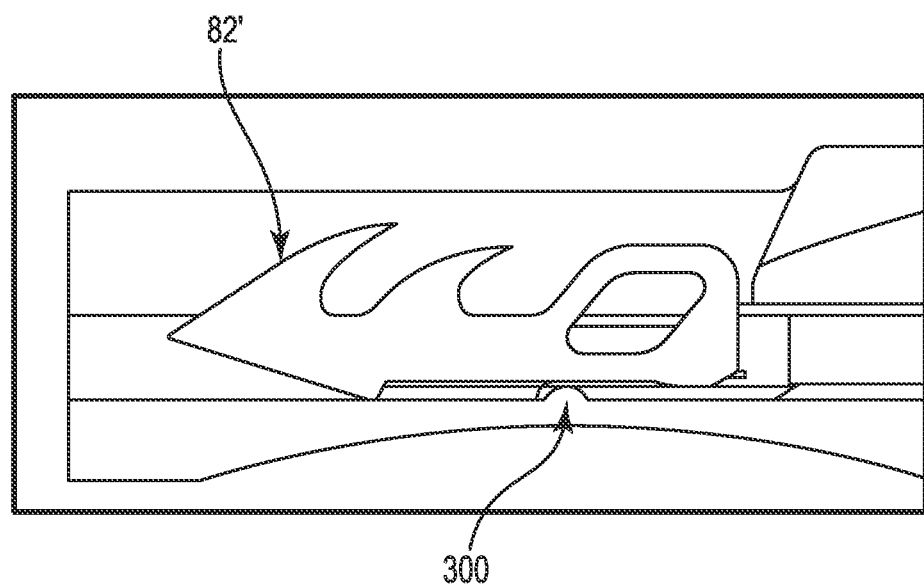
FIG. 23 is a sectional view of one embodiment of an anchor retention device holding a tissue anchor within a cannula of the delivery device.

FIG. 23 is a cross-sectional side view of one embodiment of an anchor retention feature 300 in a delivery tool. Some delivery tools can include a moveable cannula, or a stationary cannula, sized to retain the anchor 82'. In one embodiment, the anchor retention feature 300 is provided as a projection or a bump formed inside of the cannula, and the bump is adapted to engage with the anchor 82'. The engagement between the anchor retention feature 300 and the anchor 82' could be a frictional engagement, or the anchor retention feature 300 could be configured to mate with a recess formed in the anchor 82'. In one embodiment, the bump is formed on a portion of the cannula that has a cut-out relief forming a living hinge on a surface of the cannula, where the hinge portion flexes up/down as the anchor 82' pushes over or engages with the anchor retention feature 300. This embodiment combines the positive engagement of the projection with the anchor 82' and hinge motion to indicate to the user when the anchor 82' is securely engaged with the anchor retention feature 300.

Figure 24:
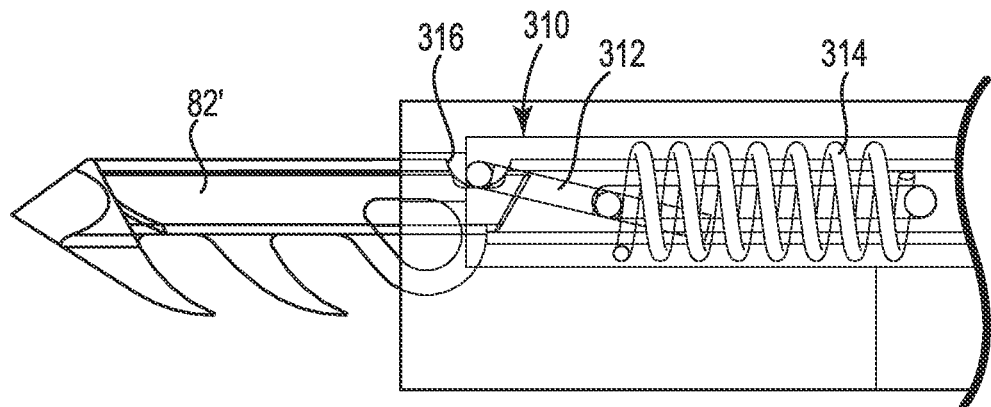
FIG. 24 is a sectional view of another embodiment of an anchor retention device holding a tissue anchor within a cannula of the delivery device.

FIG. 24 is a side view of one embodiment of an anchor retention feature 310 in a cannula of a delivery tool, where the anchor retention feature 310 is provided as a U-shaped wire 312 that is biased by a spring 314 located inside of the cannula. In one example, the U-shaped wire 312 engages with a relief 316 cut into the anchor 82'.

Figure 25:
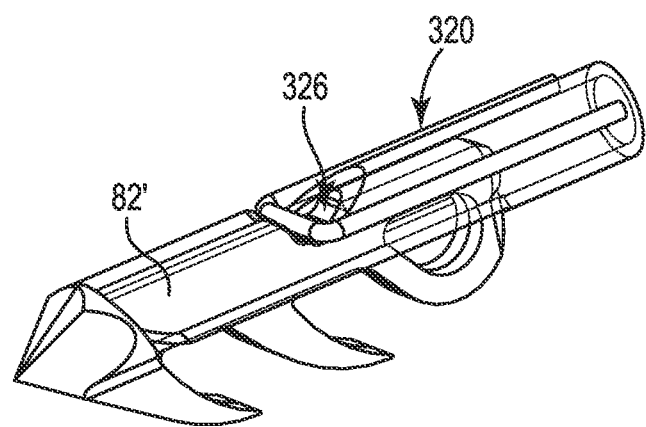
FIG. 25 is a sectional view of another embodiment of an anchor retention device holding a tissue anchor within a cannula of the delivery device.

FIG. 25 is a perspective view of one embodiment of an anchor retention feature 320 in a cannula of a delivery tool, where the anchor retention feature 320 includes a U-shaped wire 322 that flexes in a lateral direction to engage a recess 326 formed in the anchor 82'. This embodiment employs the flex of the wire 322 and does not rely on spring bias for engagement between the feature 320 and the anchor 82'.

Figure 26:
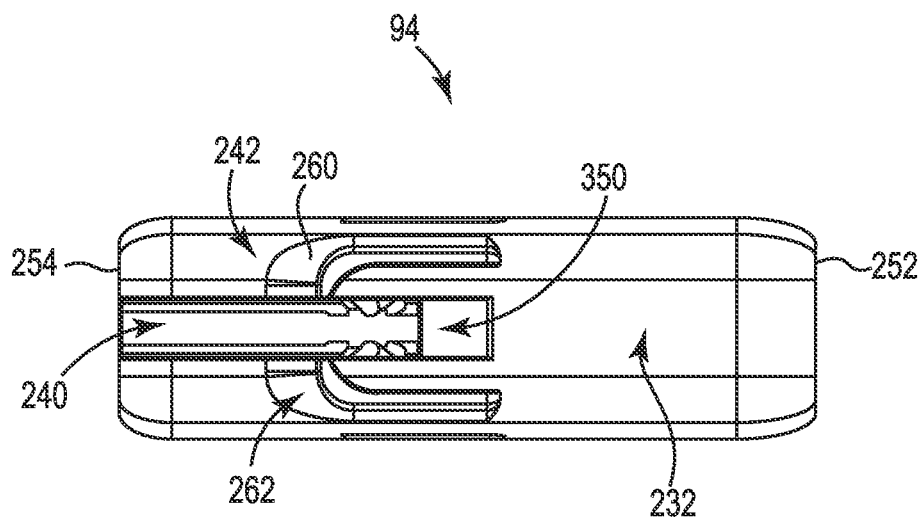
FIG. 26 is a bottom view of the distal tip showing another embodiment of an anchor retention device.
Figure 27:
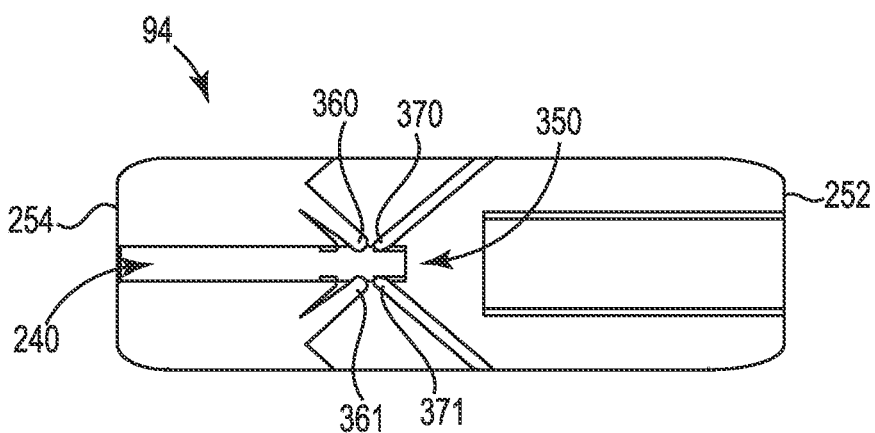
FIG. 27 is a sectional view of the anchor retention device shown in FIG. 26.

FIG. 26 is a view of the inferior side 232 of the distal tip 94 and FIG. 27 is a sectional view of one embodiment of an anchor retainer 350 for the distal tip 94 of a delivery device 70. The inferior side 232 of the distal tip 94 includes the first and second 260, 262 of the guide rails 242 that are configured to receive the sled 116 of the fixation device 60. The anchor retainer 350 includes a pair of distal engagement prongs 360, 361 and a pair of proximal engagement prongs 370, 371. The pair of distal engagement prongs 360, 361 are adapted to hold the anchor 82 back in a proximal direction, while the pair of proximal engagement prongs 370, 371 are adapted to positively engage with the body of the anchor. The engagement prongs 360, 361 and 370, 371 of the anchor retainer 350 are configured to produce an audible click when the body of the anchor 82 is pushed in a proximal direction within the slot 240. Multiple engagement prongs, for example two prongs on each side of the distal tip 94 as shown, are beneficial in ensuring that the anchor 82 is positively within the distal tip 94, since the distal tip 94 is eventually directed into the pelvis along a path that offers limited visibility.

Figure 28:
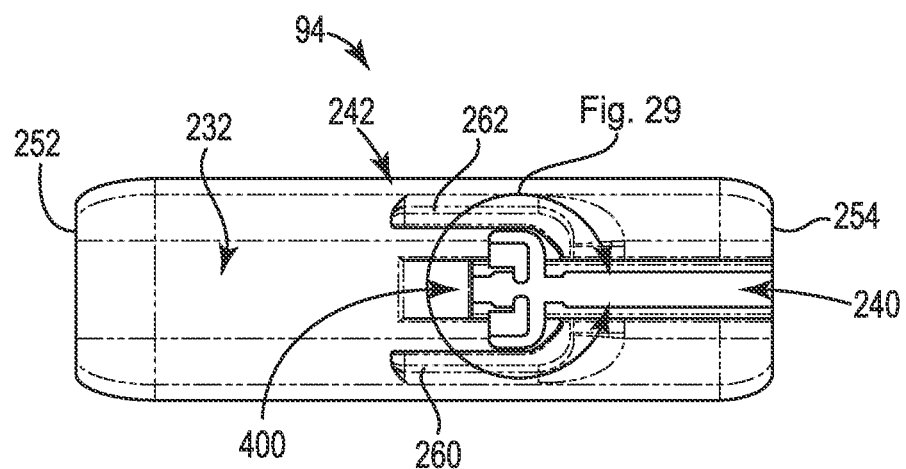
FIG. 28 is a bottom view of the distal tip showing another embodiment of an anchor retention device.
Figure 29:
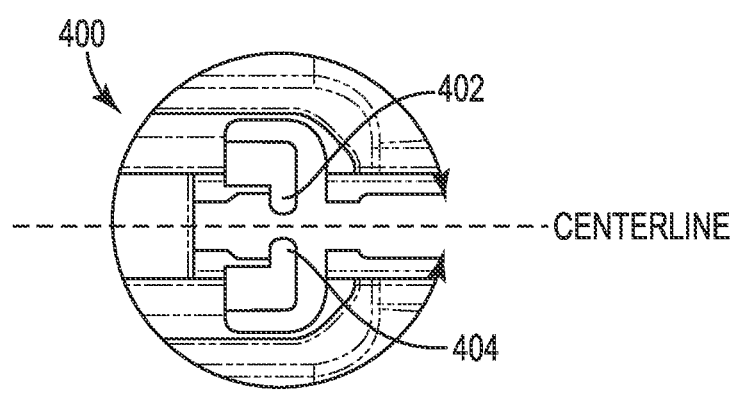
FIG. 29 is an enlarged view of the anchor retention device shown in FIG. 28.

FIG. 28 is a view of the inferior side 232 (or bottom side) of the distal tip 94 showing an anchor retainer 400, and FIG. 29 is an enlarged view of the anchor retainer 400. The anchor retainer 400 is realized by opposing side arms 402, 404 where each side arm 402, 404 is configured to flex in a lateral direction relative to the long axis of the distal tip 94. The side arms 402, 404 are adapted to flex laterally outward away from the centerline of the long axis to move out of the way as the anchor 82 is slid proximally within the slot 240, and thereafter, the side arms 402, 404 flex laterally inward toward the centerline of the long axis to engage and grasp the eyelet 128 (FIG. 3) of the anchor 82 to hold the anchor 82 securely within the distal tip 94.

The slot 240 is about 2.2 mm wide, and the spacing between the opposed arms 402, 404 is about 0.55 mm, which allows the anchor retainer 400 to securely engage within the eyelet 128 of the anchor 82.

Figure 30A:
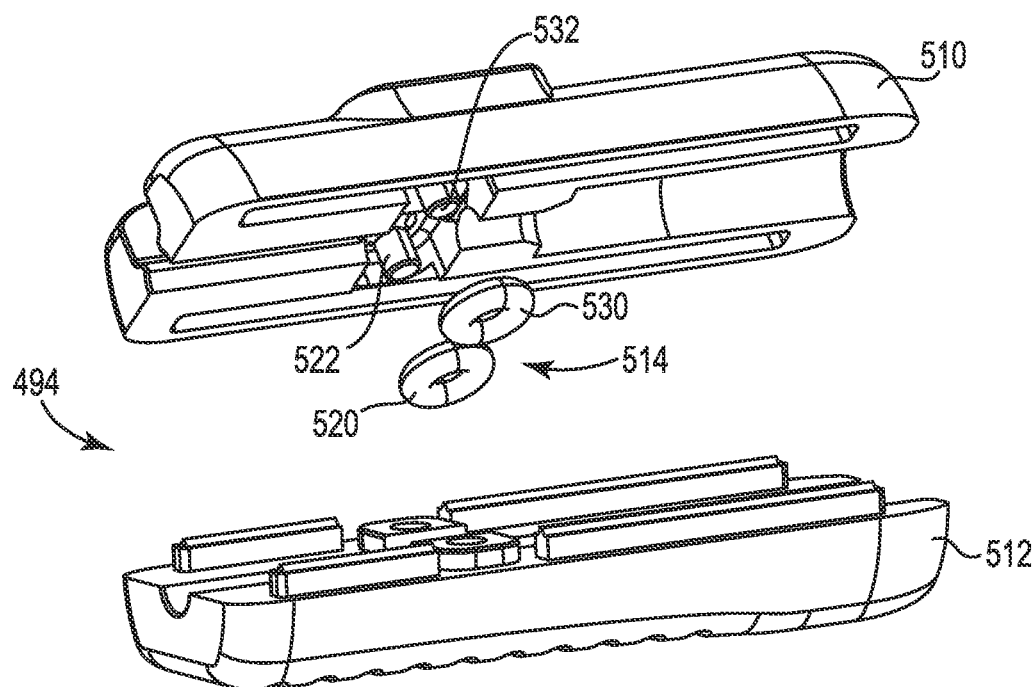
FIG. 30A is an exploded view of a distal tip of a delivery device showing another embodiment of an anchor retention device.
Figure 30B:
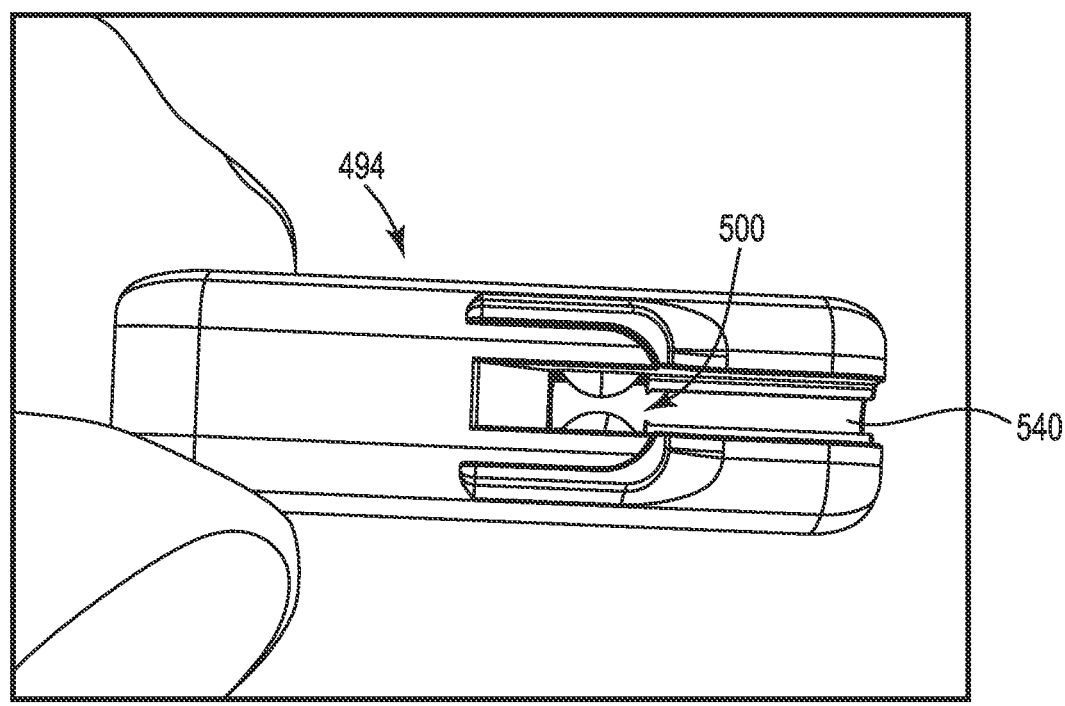
FIG. 30B is a bottom view of the assembled distal tip shown in FIG. 30A.

FIG. 30A is an exploded view and FIG. 30B is a view of an inferior side (or bottom side) view of one embodiment of another distal tip 494 including an anchor retainer 500.

Figure 30C:
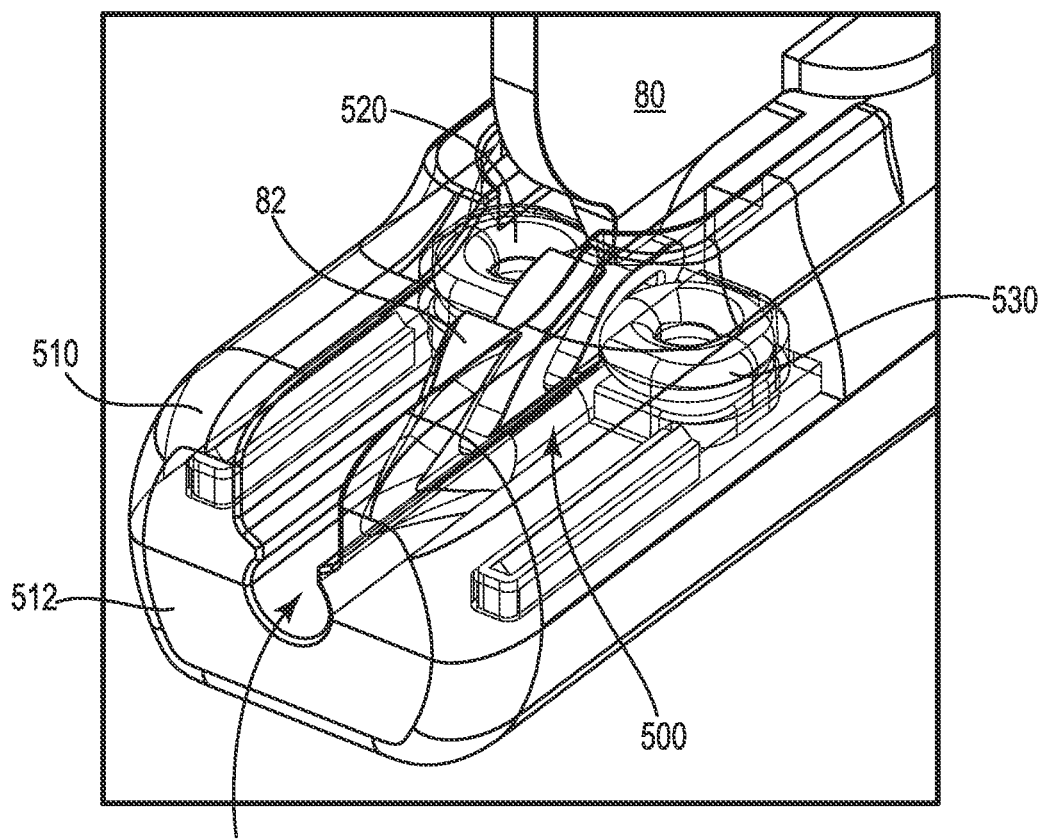
FIG. 30C is a perspective view of the distal tip showing a tissue anchor retained by the anchor retention device of FIG. 30A.

FIG. 30C is a perspective view of the distal tip 494 shown in FIG. 30B with the tissue fixation device 60 of FIG. 2 engaged with the anchor retainer 500.

The distal tip 494 incudes a top shell portion 510 that mates with a bottom shell portion 512 to capture a pair of elastomer toroids 514. A first toroid 520 is secured to a first pin 522 formed inside of the top shell portion 510, and a second toroid 530 is secured to a second pin 532 formed inside of the top shell portion 510.

When assembled, the distal tip 494 includes a slot 540 sized to receive and deliver the anchor 82 (FIG. 2). The slot has a width of about 2.2 mm, and the opposing toroids 520, 530 are spaced apart by about 0.55 mm to ensure that the anchor retainer pinches into, and engages with, the eyelet 128 of the anchor 82. Other anchor retainers include a more complicated manufacturing approach, or close machine tolerances to make metal or plastic retainers. In contrast, the anchor retainer 500 can be realized through a pair of elastomeric O-rings that sustain repeated and repeatable cycling of engagement with anchors 82. The two-part or split shells 510, 512 of the housing allow for easy and accurate placement of the toroidal O-rings onto the pins 522, 532. The toroidal O-rings advantageously will not damage or negatively affect the suture 82 that passes through the eyelet 128 of the anchor 82, and testing of this prototype has shown good ability to retain the anchor 82 after repeated cycling.

Figure 31:
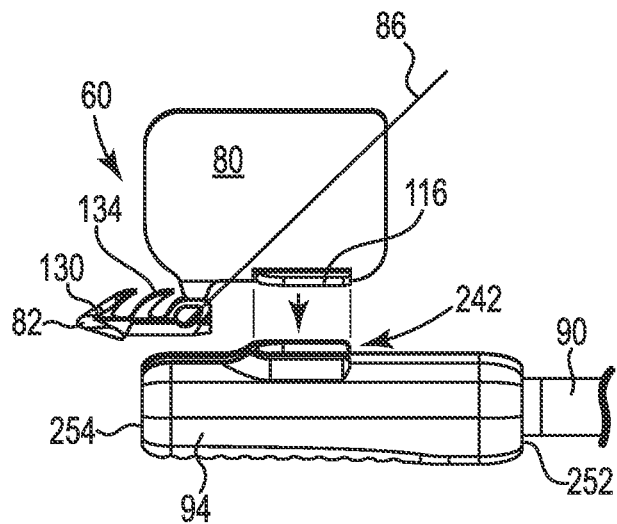
FIG. 31 is a side view of the fixation device shown in FIG. 3 ready for placement onto a bottom inferior face of the distal tip of the delivery device shown in FIG. 13.

FIGS. 31-32F describe a position of the tissue fixation device 60 relative to the distal tip 94 during use of the system 50, which relate to the following Instructions for Use.

Instructions for Use for the Tissue Anchor System 50
1. Select the desired suture size 0 or smaller (suture is not included).
2. Load up to two sutures into the anchor eyelet.

Figures 32A, 32B:
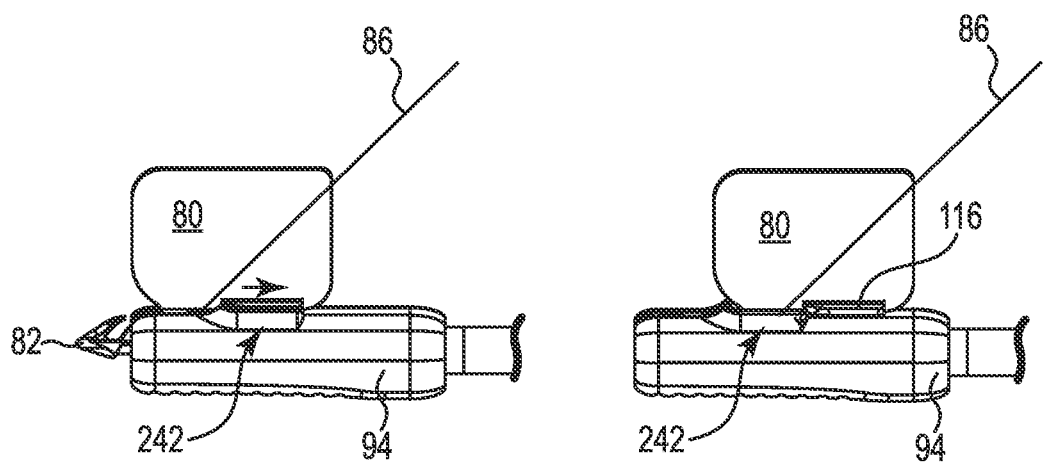
FIG. 32A is a side view of the fixation device of FIG. 31 placed on the bottom inferior face of the distal tip.
FIG. 32B is a side view of the fixation device of FIG. 32A displaced in a proximal direction (i.e., to the right) to engage the tissue anchor with an anchor retention device of the distal tip.

3. FIG. 31: Grasp the anchor tab 80 and suture 86, keeping the suture 86 tensioned proximally away from the anchor barbs 130, 134. Line up the sled 116 of the anchor tab 80 with the loading or guide rails 242 on the distal tip 94 of the delivery device.
4. FIG. 32A-32B: Slide the anchor 82 back (in a proximal direction) into the anchor retainer 400 (as one example) until a click is heard and/or felt. In this position, the sled 116 of the anchor tab 80 should be completely outside the loading guide rails 242 (See FIG. 32D).
5. FIG. 32C-32D: With the anchor 82 aligned along a horizontal axis, twist the anchor tab 80 in either a clockwise or a counterclockwise direction relative to the vertical axis (e.g., like a key in a lock) to break the tab 80 away from the anchor 82. Discard the anchor tab 80. (Note: if twisting is difficult, the anchor 82 may not be slid all the way back in the proximal direction, which will cause the sled 116 to contact and bind with the rails 242, as illustrated in the improper alignment shown in FIG. 32E).
6. FIG. 32F: The anchor 82 is now fully loaded and is ready to be inserted into tissue. The anchor 82 should not extend from the distal end 254 of the distal tip 94 or be loose inside the cannula; if it is, gently pull the sutures 86 in a proximal direction to seat the anchor 82 in the anchor retainers 500 (as one example). Avoid excessive force on the suture 86 as this may dislodge the anchor.
7. Place the distal tip 94 of the delivery tool 70 at the desired tissue fixation point, for example by using finger guidance.
8. Once in position, maintain pressure on the tissue fixation point and press the plunger 96 on the handle 92 of the delivery tool 70 (FIG. 1) until a click is felt to indicate the plunger 96 is fully engaged.
9. Release the plunger 96 and ensure it returns to its original, starting position.
10. Withdraw the delivery device 70 from the patient. Confirm the anchor 82 and the suture 86 were placed in the desired location by palpating with a finger.
11. If it is determined the anchor position is undesirable, remove the suture 86 from the anchor 82 and repeat steps 1-10, leaving the anchor 82 in vivo.
12. Ensure the suture 86 is secured with an appropriate knot tying technique. The knot tying may be delayed until all desired anchors are placed.
13. Trim the excess suture.
14. To place additional anchors, rinse the head of the delivery device 70 in sterile saline or antibiotic solution to remove particulates, and repeat steps 1-10.

Figure 33:
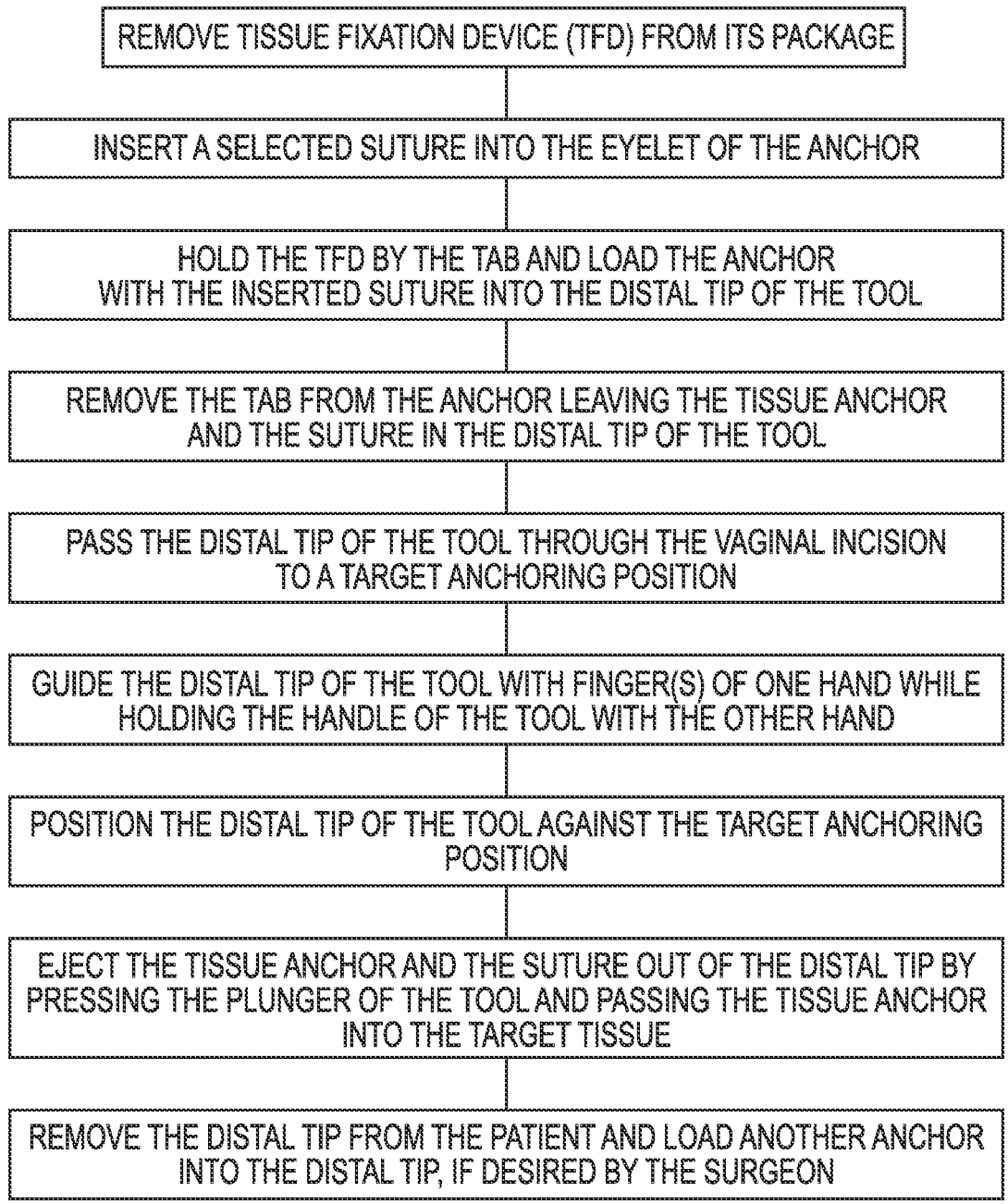
FIG. 33 is a diagram of one embodiment of instructions for loading a fixation device into a distal tip of a delivery device.

FIG. 33 is a listing of steps of one method of placing an anchor into tissue. The method includes the steps where a healthcare provided removes a fixation device from its package. The surgeon selects a suture and inserts the selected suture into an eyelet of the fixation device. The surgeon or an assistant holds the fixation device by the loading tab and loads the fixation device and the inserted suture into the distal tip of the tool. The tab is removed from the fixation device leaving the tissue anchor and the suture in the distal tip of the tool. The surgeon then passes the distal tip of the tool to a target anchoring position and guides the distal tip of the tool with finger(s) of one hand while holding the handle of the tool with the other hand. The surgeon positions the distal tip of the tool against the target anchoring position and ejects the tissue anchor and the suture out of the distal tip by pressing the plunger of the tool to pass the tissue anchor into the target tissue. The anchor is thus engaged with tissue at the desired location, and the surgeon removes the distal tip from the patient and loads another fixation device into the distal tip, if desired.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention is limited only by its claims and their equivalents.

What is claimed is:

1. A fixation device comprising:
    a tissue anchor comprising a body extending longitudinally between a nose of the tissue anchor and a tail of the tissue anchor, with the nose having a pointed distal end adapted to penetrate tissue and the tail forming an eyelet sized to receive a strand of suture;
    a tab connected to the tissue anchor, with the tab having a distal side opposed to a proximal side and a superior side opposed to an inferior side; and
    a break wedge connected between the inferior side of the tab and the tissue anchor, where the break wedge is adapted to allow the tab to be snapped apart from the tail of the tissue anchor;
    wherein the tab comprises a first flange connected to and co-planar with the inferior side of the tab, with the first flange projecting in a lateral direction away from a first face of the tab.

2. The fixation device of claim 1, wherein the tab comprises a sled comprising a second flange connected to the inferior side of the tab opposite of the first flange, with the second flange projecting in a lateral direction away from a second face of the tab that is opposite of the first face of the tab.

3. The fixation device of claim 2, wherein the sled is planar, and co-planar with the inferior side of the tab, such that the sled defines a bottom-most inferior surface of the tab.

4. The fixation device of claim 2, wherein a width of the sled is wider than a width of the tissue anchor such that the width of the sled defines a widest-most aspect of the fixation device.

5. The fixation device of claim 1, wherein the nose comprises:
    a first barb integrated with the pointed distal end; and
    a blade integrated with the pointed distal end on an opposing side of the nose opposite from the first barb.

6. The fixation device of claim 1, wherein the nose comprises:
    a first barb integrated with the pointed distal end; and
    a second barb located between the first barb and the tail of the tissue anchor.

7. The fixation device of claim 1 comprising more than one barb and less than three barbs.

8. The fixation device of claim 1, wherein the tissue anchor has an anchor length measured between the pointed distal end and the tail, and a longitudinal length of the tab measured between the distal side and the proximal side of the tab is greater than the anchor length.

9. The fixation device of claim 1, wherein the tissue anchor has an anchor length measured between the pointed distal end and the tail, and a height of the tab measured between the superior side and the inferior side of the tab is greater than the anchor length.

10. The fixation device of claim 1, wherein the tissue anchor has an anchor length measured between the pointed distal end and the tail, and a longitudinal length of the tab and a height of the tab are both greater than the anchor length.

11. The fixation device of claim 1, wherein the tab has a tab width measured between the first face and an opposite second face of the tab, and the first flange
projects in the lateral direction away from the first face of the tab by a distance that is greater than the tab width.

12. The fixation device of claim 1, wherein the break wedge is connected between the inferior side of the tab and the tail of the tissue anchor.

13. The fixation device of claim 1, wherein a width of the break wedge measured at a location where the break wedge is connected to the tail is less than a width of the tab and less than a width of the tail.

14. A fixation device comprising:
a tissue anchor comprising a pointed distal end adapted to penetrate tissue, a barb adapted to engage the tissue, and an eyelet sized to receive a strand of suture; and
a tab connected to the tissue anchor, with the tab having a distal side opposed to a proximal side and a superior side opposed to an inferior side, and a break wedge connecting the tab to a proximal portion of the tissue anchor, where the break wedge is adapted to allow the tab to be snapped apart from the tissue anchor;
wherein the tab comprises a sled comprising a first flange coplanar with the inferior side of the tab and projecting in a first lateral direction away from a first face of the tab, and a second flange coplanar with the inferior side of the tab and projecting in a second lateral direction away from a second face of the tab.

15. A fixation device comprising:
a tissue anchor comprising a distal end adapted to penetrate tissue and a proximal tail end forming an eyelet sized to receive a strand of suture; and
a tab connected to the tissue anchor, with the tab having a first lateral face and an opposing second lateral face and a break wedge connected between the tab and the proximal tail end of the tissue anchor, where the break wedge is adapted to allow theta to be snapped apart from the proximal tail end of the tissue anchor; and
a first flange connected to the first lateral face and projecting in a first lateral direction away from the first lateral face.

16. The tissue fixation device of claim 15, further comprising a sled connected to the tissue anchor, with the sled comprising the first flange and a second flange, with the second flange connected to the second lateral face and projecting in a second lateral direction away from the second lateral face.

17. The tissue fixation device of claim 15, wherein the first flange is orthogonal relative to the first lateral face and the second flange is orthogonal relative to the second lateral face.

18. A tissue anchor system comprising:
a fixation device including a tab connected to a tissue anchor, where the tab includes a sled comprising opposing first and second flanges projecting laterally from opposing first and second faces, respectively, of the tab, and a break wedge separate from the sled and connected between an inferior side of the tab and the tissue anchor, where the break wedge is adapted to allow the tab to be snapped apart from the tissue anchor; and
a tool provided to insert the tissue anchor into tissue, with the tool including a shaft connected between a proximal handle portion and a distal tip;
wherein the distal tip comprises a face extending between a proximal end and a distal end of the distal tip, with a slot formed in the face that is sized to receive the tissue anchor, and a rail projecting away from the face of the distal tip;
wherein the rail limits movement of the sled of the fixation device in a distal direction for alignment of the tissue anchor within the slot.

19. The tissue anchor system of claim 18, wherein the rail comprises a first wall formed on the face of the distal tip and a second wall formed on the face of the distal tip, with the first wall parallel to the distal end face of the distal tip.

20. The tissue anchor system of claim 18, wherein the rail comprises a first wall formed on the face of the distal tip and a second wall formed on the face of the distal tip, with the second wall orthogonal to the distal end face of the distal tip.

21. The tissue anchor system of claim 18, wherein the rail comprises a first wall formed on the face of the distal tip and a second wall formed on the face of the distal tip, with the first wall connected to the second wall.

22. The tissue anchor system of claim 18, wherein the rail comprises a first wall formed on the face of the distal tip, with the first wall parallel to the distal end face of the distal tip, and a pair of walls orthogonal to the distal end face of the distal tip and connected to the first wall, with the first wall and the pair of walls arranged in a U-shape.

23. A fixation device comprising:
a tissue anchor comprising a body extending longitudinally between a nose of the tissue anchor and a tail of the tissue anchor, with the nose having a pointed distal end adapted to penetrate tissue and the tail forming an eyelet sized to receive a strand of suture; and
a tab connected to the tissue anchor, with the tab having a distal side opposed to a proximal side and a superior side opposed to an inferior side, and the tab is adapted to be separated from the tissue anchor;
wherein the tab comprises a first flange connected to and co-planar with the inferior side of the tab, with the first flange projecting in a lateral direction away from a first face of the tab;
wherein the tissue anchor has an anchor length measured between the pointed distal end and the tail, and a longitudinal length of the tab measured between the distal side and the proximal side of the tab is greater than the anchor length.

24. A fixation device comprising:
a tissue anchor comprising a body extending longitudinally between a nose of the tissue anchor and a tail of the tissue anchor, with the nose having a pointed distal end adapted to penetrate tissue and the tail forming an eyelet sized to receive a strand of suture; and
a tab connected to the tissue anchor, with the tab having a distal side opposed to a proximal side and a superior side opposed to an inferior side, and the tab is adapted to be separated from the tissue anchor;
wherein the tab comprises a first flange connected to and co-planar with the inferior side of the tab, with the first flange projecting in a lateral direction away from a first face of the tab;
wherein the tissue anchor has an anchor length measured between the pointed distal end and the tail, and a height of the tab measured between the superior side and the inferior side of the tab is greater than the anchor length.

25. A fixation device comprising:
a tissue anchor comprising a body extending longitudinally between a nose of the tissue anchor and a tail of the tissue anchor, with the nose having a pointed distal end adapted to penetrate tissue and the tail forming an eyelet sized to receive a strand of suture; and
a tab connected to the tissue anchor, with the tab having a distal side opposed to a proximal side and a superior side opposed to an inferior side, and the tab is adapted to be separated from the tissue anchor;
wherein the tab comprises a first flange connected to and co-planar with the inferior side of the tab, with the first flange projecting in a lateral direction away from a first face of the tab;
wherein the tissue anchor has an anchor length measured between the pointed distal end and the tail, and a longitudinal length of the tab and a height of the tab are both greater than the anchor length.

* * * * *